(12) United States Patent
Granz et al.

(10) Patent No.: US 11,648,134 B2
(45) Date of Patent: *May 16, 2023

(54) PROSTHETIC ATTACHMENT SYSTEM

(71) Applicant: OSSUR ICELAND EHF, Reykjavik (IS)

(72) Inventors: Dadi Granz, Reykjavik (IS); Martin Lund Storup, Reykjavik (IS); Andrew Bache, Reykjavik (IS); Linda Ros Birgisdottir, Reykjavik (IS); Egill Sveinbjorn Egilsson, Reykjavik (IS); Lukas Kalemba, Reykjavik (IS); Eelco Dolfsma, Reykjavik (IS)

(73) Assignee: OSSUR ICELAND EHF, Reykjavik (IS)

( * ) Notice: Subject to any disclaimer, the term of this patent is extended or adjusted under 35 U.S.C. 154(b) by 91 days.

This patent is subject to a terminal disclaimer.

(21) Appl. No.: 17/092,895

(22) Filed: Nov. 9, 2020

(65) Prior Publication Data

US 2021/0052400 A1 Feb. 25, 2021

Related U.S. Application Data

(63) Continuation of application No. 15/984,776, filed on May 21, 2018, now Pat. No. 10,828,180.

(Continued)

(51) Int. Cl.
| | | |
|---|---|---|
| *A61F 2/78* | (2006.01) | |
| *A61F 2/80* | (2006.01) | |
| *A61F 2/66* | (2006.01) | |
| *A61F 2/76* | (2006.01) | |
| *A61F 2/60* | (2006.01) | |
| *F16B 21/16* | (2006.01) | |
| *A61F 2/50* | (2006.01) | |

(52) U.S. Cl.
CPC .............. *A61F 2/7812* (2013.01); *A61F 2/60* (2013.01); *A61F 2/66* (2013.01); *A61F 2/76* (2013.01);

(Continued)

(58) Field of Classification Search
CPC ................ A61F 2/80; A61F 2002/7831; A61F 2002/7875

See application file for complete search history.

(56) References Cited

U.S. PATENT DOCUMENTS

| 980,457 A | 1/1911 | Toles |
|---|---|---|
| 1,398,824 A | 11/1921 | Abrams |

(Continued)

FOREIGN PATENT DOCUMENTS

| DE | 745981 C | 5/1944 |
|---|---|---|
| DE | 813190 C | 7/1949 |

(Continued)

OTHER PUBLICATIONS

International Search Report from PCT Application No. PCT/US2018/058625, dated Feb. 11, 2019.

(Continued)

*Primary Examiner* — David H Willse
(74) *Attorney, Agent, or Firm* — Workman Nydegger

(57) ABSTRACT

A prosthetic attachment system includes an insert arranged for connection to a prosthetic liner, and an attachment unit arranged for connection to a distal end of a prosthetic socket. The attachment unit comprises a body defining an axis and a central opening for selectively receiving the insert. The body carries a plurality of locking elements that are distributed circumferentially about the axis and radially repositionable relative to the axis. A release mechanism is slidably positioned on an outer surface of the body to move the prosthetic attachment system between a locked configuration in which the locking elements are radially repositioned to lock the insert in the central opening of the body and an unlocked configuration in which the insert is released from the central opening.

15 Claims, 7 Drawing Sheets

Related U.S. Application Data

(60) Provisional application No. 62/597,198, filed on Dec. 11, 2017, provisional application No. 62/509,246, filed on May 22, 2017.

(52) U.S. Cl.
CPC .............. *A61F 2/80* (2013.01); *F16B 21/165* (2013.01); *A61F 2002/5069* (2013.01); *A61F 2002/5072* (2013.01); *A61F 2002/5075* (2013.01); *A61F 2002/5087* (2013.01); *A61F 2002/5092* (2013.01); *A61F 2002/607* (2013.01); *A61F 2002/7837* (2013.01); *A61F 2002/7875* (2013.01)

(56) References Cited

U.S. PATENT DOCUMENTS

| | | |
|---|---|---|
| 1,893,853 A | 1/1933 | Tullis |
| 2,530,285 A | 11/1950 | Catranis |
| 2,533,404 A | 12/1950 | Sharp et al. |
| 2,634,424 A | 4/1953 | Gorman |
| 2,671,225 A | 3/1954 | Schoene et al. |
| 2,808,593 A | 10/1957 | Andersen |
| 3,393,407 A | 7/1968 | Kandel |
| 3,671,980 A | 6/1972 | Baird |
| 4,216,550 A | 8/1980 | Thompson |
| 4,564,365 A | 1/1986 | Winer et al. |
| 4,923,474 A | 5/1990 | Klasson et al. |
| 4,938,775 A | 7/1990 | Morgan |
| 5,007,937 A | 4/1991 | Fishman et al. |
| 5,139,523 A | 8/1992 | Paton et al. |
| 5,163,965 A | 11/1992 | Rasmusson et al. |
| 5,226,918 A | 7/1993 | Silagy et al. |
| 5,314,496 A | 5/1994 | Harris et al. |
| 5,376,129 A | 12/1994 | Faulkner et al. |
| 5,376,131 A | 12/1994 | Lenze et al. |
| 5,413,392 A | 5/1995 | Schlack et al. |
| 5,507,837 A | 4/1996 | Laghi |
| 5,549,709 A | 8/1996 | Caspers |
| 5,593,454 A | 1/1997 | Helmy |
| 5,658,353 A | 8/1997 | Layton |
| 5,662,715 A | 9/1997 | Slemker |
| 5,702,489 A | 12/1997 | Slemker |
| 5,718,925 A | 2/1998 | Kristinsson et al. |
| 5,728,170 A | 3/1998 | Becker et al. |
| 5,735,906 A | 4/1998 | Caspers |
| 5,882,053 A | 3/1999 | Bekins et al. |
| 5,888,216 A | 3/1999 | Haberman |
| 5,904,722 A | 5/1999 | Caspers |
| 5,931,872 A | 8/1999 | Lohmann |
| 5,972,036 A | 10/1999 | Kristinsson et al. |
| 6,063,125 A | 5/2000 | Arbogast et al. |
| 6,106,559 A | 6/2000 | Meyer |
| 6,123,340 A | 9/2000 | Sprafka et al. |
| 6,149,691 A | 11/2000 | Fay et al. |
| 6,231,616 B1 | 5/2001 | Helmy |
| 6,231,617 B1 | 5/2001 | Fay |
| 6,273,918 B1 | 8/2001 | Yuhasz et al. |
| 6,287,345 B1 | 9/2001 | Slemker et al. |
| 6,334,876 B1 | 1/2002 | Perkins |
| 6,361,568 B1 | 3/2002 | Hoerner |
| 6,402,789 B1 | 6/2002 | Gramnas |
| 6,440,173 B1 | 8/2002 | Meyer |
| 6,508,842 B1 | 1/2003 | Caspers |
| 6,554,868 B1 | 4/2003 | Caspers |
| 6,585,774 B2 | 7/2003 | Dean, Jr. et al. |
| 6,645,253 B2 | 11/2003 | Caspers |
| 6,726,726 B2 | 4/2004 | Caspers |
| 6,761,742 B2 | 7/2004 | Caspers |
| 7,056,303 B2 | 6/2006 | Dennis et al. |
| 7,234,108 B1 | 6/2007 | Carstens |
| 7,351,367 B2 | 4/2008 | Swanson, Sr. |
| 7,427,297 B2 | 9/2008 | Patterson et al. |
| 7,427,298 B1 | 9/2008 | Swanson, Sr. |
| 7,637,958 B2 | 12/2009 | Coop |
| 7,771,487 B2 | 8/2010 | Mantelmacher |
| 8,211,187 B2 | 7/2012 | Slemker et al. |
| 8,795,385 B2 | 8/2014 | Bache |
| 8,801,803 B2 | 8/2014 | Song et al. |
| 9,050,202 B2 | 6/2015 | Bache et al. |
| 9,198,778 B2 | 12/2015 | Celebi et al. |
| 9,248,033 B2 | 2/2016 | Bache |
| 10,828,180 B2 * | 11/2020 | Granz ...................... A61F 2/66 |
| 2001/0005798 A1 | 6/2001 | Caspers |
| 2001/0016781 A1 | 8/2001 | Caspers |
| 2002/0040248 A1 | 4/2002 | Karason |
| 2002/0087215 A1 | 7/2002 | Caspers |
| 2002/0091449 A1 | 7/2002 | Caspers et al. |
| 2002/0099450 A1 | 7/2002 | Dean, Jr. et al. |
| 2003/0191539 A1 | 10/2003 | Caspers |
| 2003/0195636 A1 * | 10/2003 | Coop ...................... A61F 2/80 623/36 |
| 2004/0030411 A1 | 2/2004 | Caspers |
| 2004/0098136 A1 | 5/2004 | Caspers |
| 2004/0122528 A1 | 6/2004 | Egilsson |
| 2004/0143345 A1 | 7/2004 | Caspers |
| 2004/0167638 A1 | 8/2004 | Caspers |
| 2004/0181290 A1 | 9/2004 | Caspers |
| 2004/0236434 A1 | 11/2004 | Carstens |
| 2004/0243251 A1 | 12/2004 | Carstens |
| 2005/0244220 A1 | 11/2005 | Ingimarsson |
| 2007/0055383 A1 | 3/2007 | King |
| 2011/0307080 A1 | 12/2011 | Perkins et al. |
| 2012/0310371 A1 | 12/2012 | Bachus et al. |
| 2013/0173020 A1 | 7/2013 | Slemker et al. |
| 2013/0195540 A1 | 8/2013 | Wozencroft et al. |
| 2013/0282143 A1 | 10/2013 | Perkins et al. |
| 2015/0230945 A1 | 8/2015 | Bache et al. |
| 2016/0000584 A1 | 1/2016 | Brown |
| 2016/0038314 A1 | 2/2016 | Kuiken et al. |
| 2016/0120665 A1 | 5/2016 | Muller |
| 2016/0331562 A1 | 11/2016 | Bache et al. |

FOREIGN PATENT DOCUMENTS

| | | |
|---|---|---|
| DE | 1795809 U | 9/1959 |
| DE | 2060239 A1 | 6/1972 |
| DE | 2540138 A1 | 3/1977 |
| DE | 2729800 A1 | 1/1979 |
| DE | 3221920 A1 | 4/1983 |
| DE | 3508919 A1 | 9/1986 |
| DE | 9419208 U1 | 1/1995 |
| DE | 202005018109 U1 | 3/2006 |
| DE | 102008029732 A1 | 1/2010 |
| GB | 267988 | 9/1925 |
| GB | 2069847 A | 9/1981 |
| GB | 2087727 A | 6/1982 |
| GB | 2338899 A | 1/2000 |
| GB | 2479532 A | 10/2011 |
| JP | 07-155343 A | 6/1995 |
| NL | 2010991 C | 12/2014 |
| RU | 2079292 C1 | 5/1997 |
| WO | 0074611 A2 | 12/2000 |
| WO | 0154631 A1 | 8/2001 |
| WO | 03024367 A2 | 3/2003 |
| WO | 03024370 A1 | 3/2003 |
| WO | 03039398 A1 | 3/2003 |
| WO | 03099173 A1 | 12/2003 |

OTHER PUBLICATIONS

International Search Report from PCT Application No. PCT/US2018/033633, dated Nov. 22, 2018.

* cited by examiner

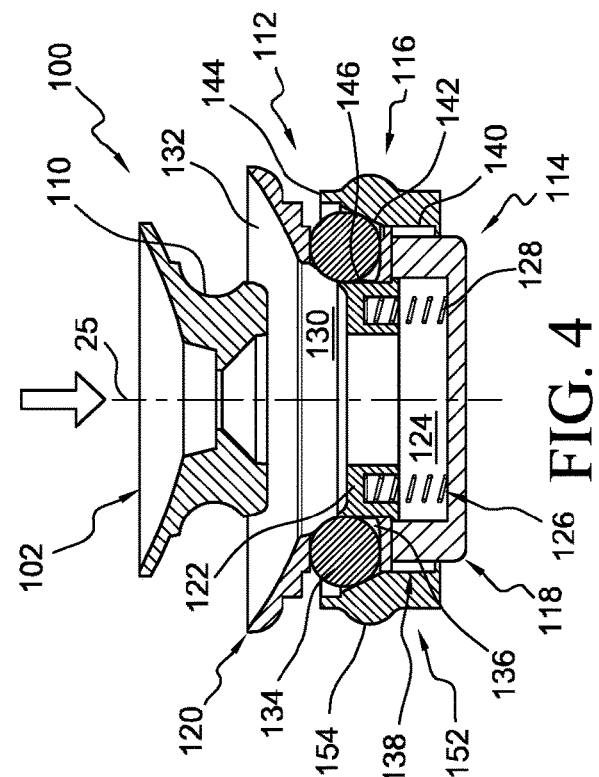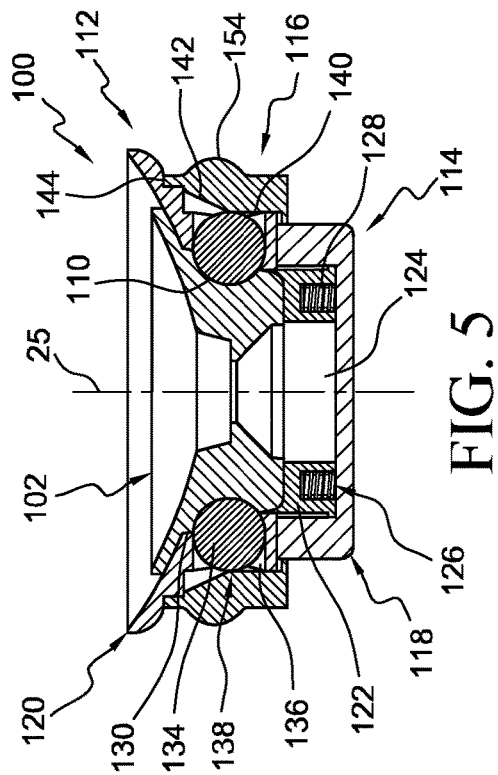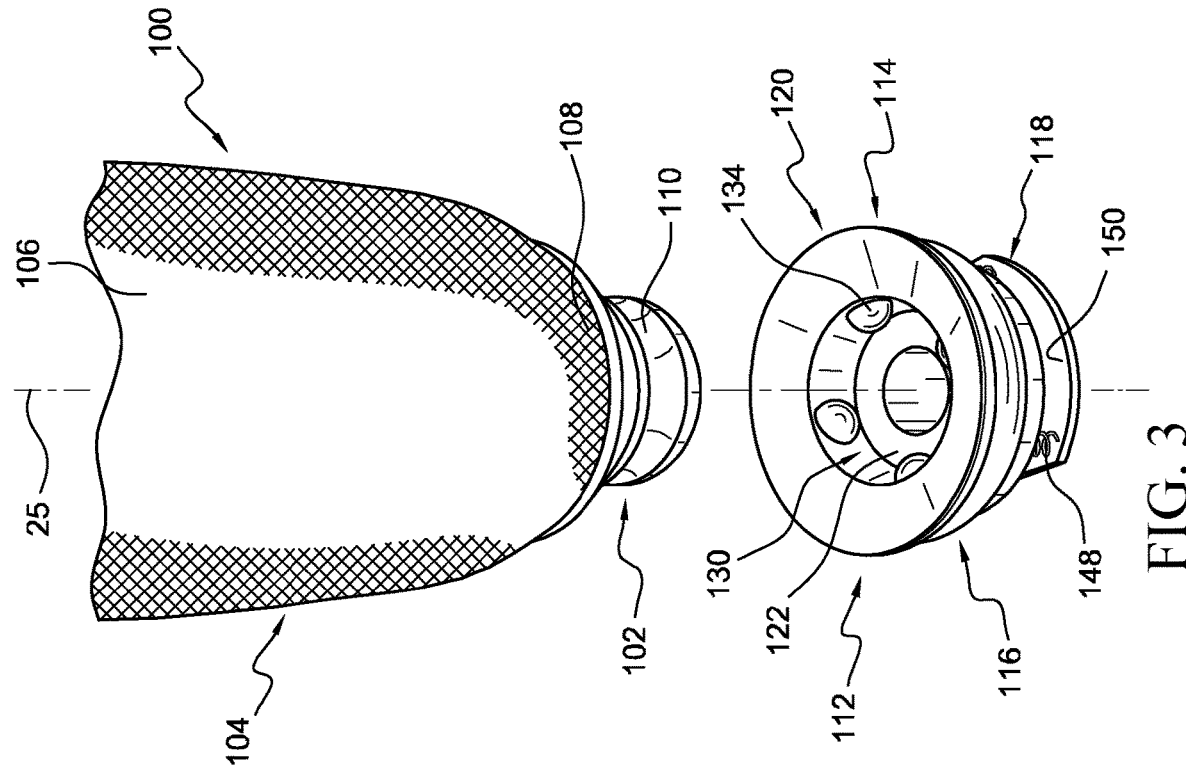

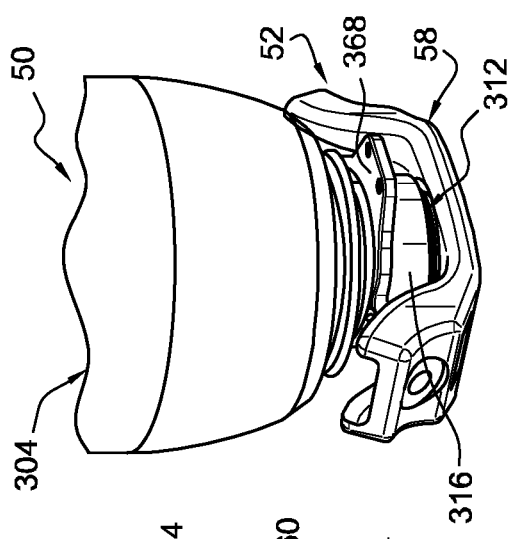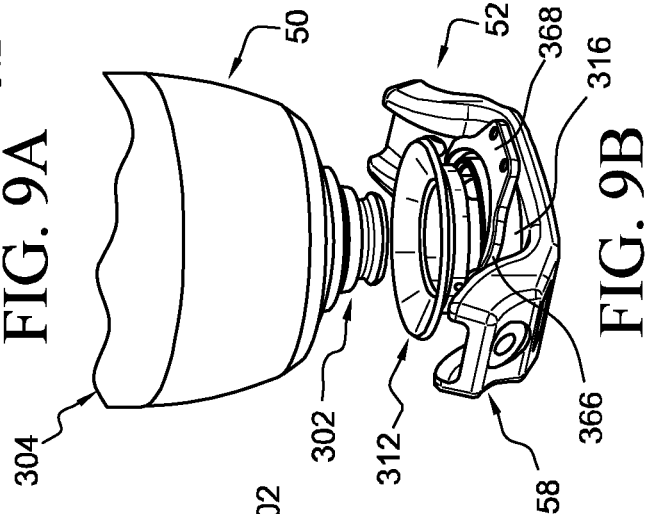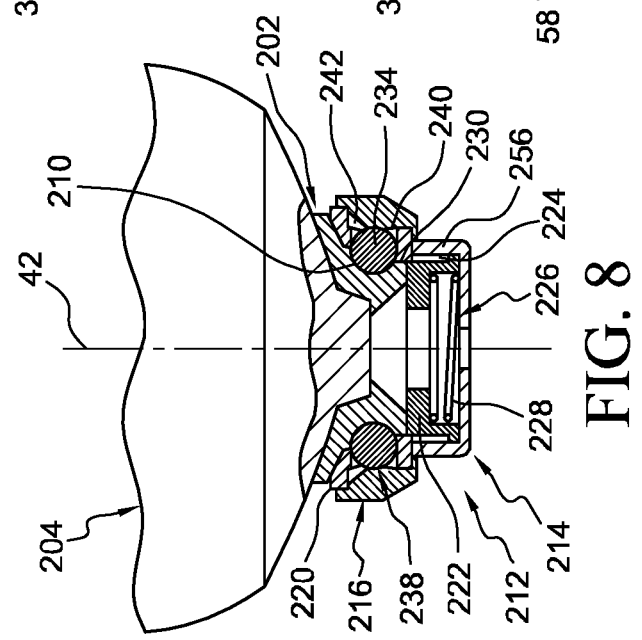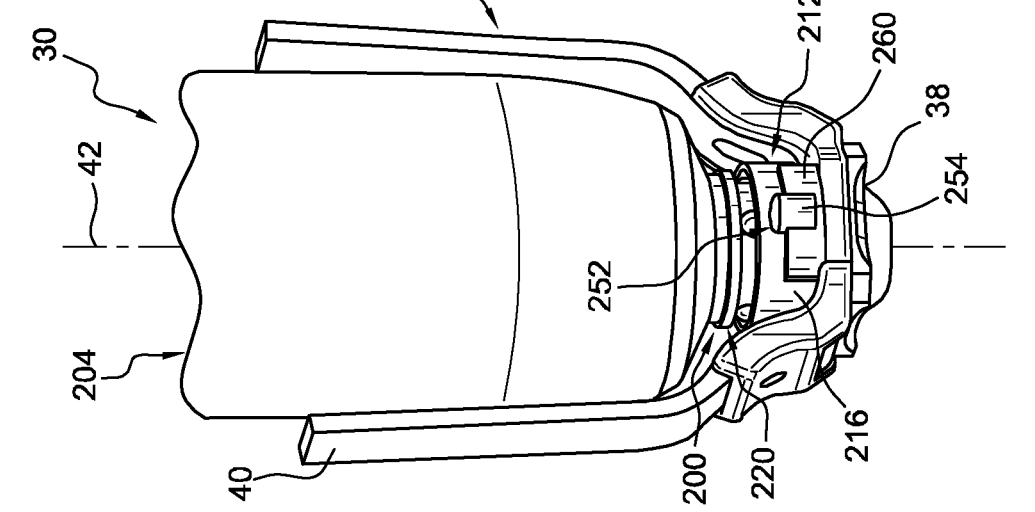

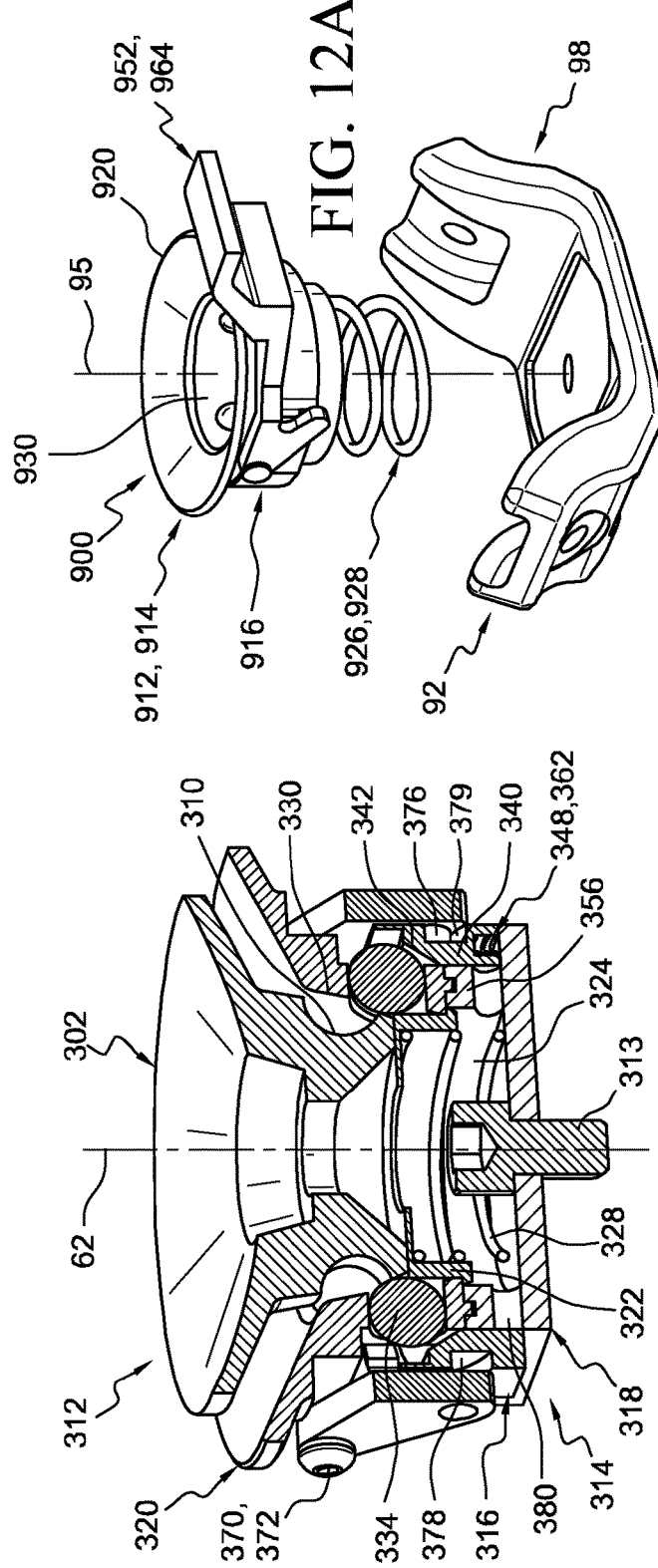

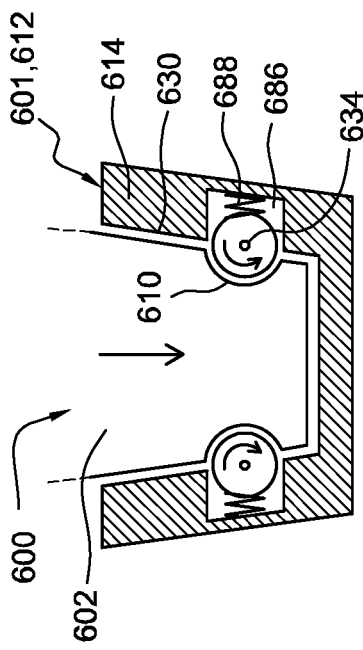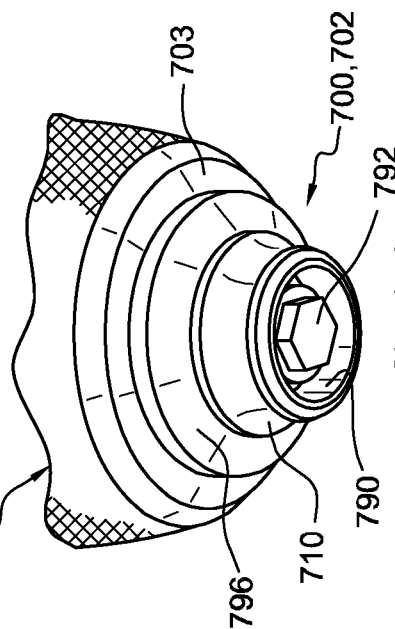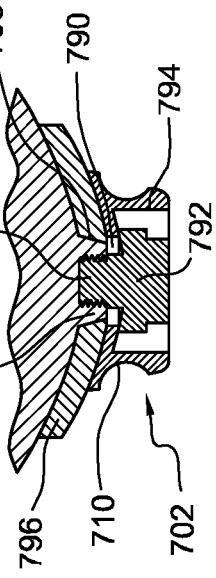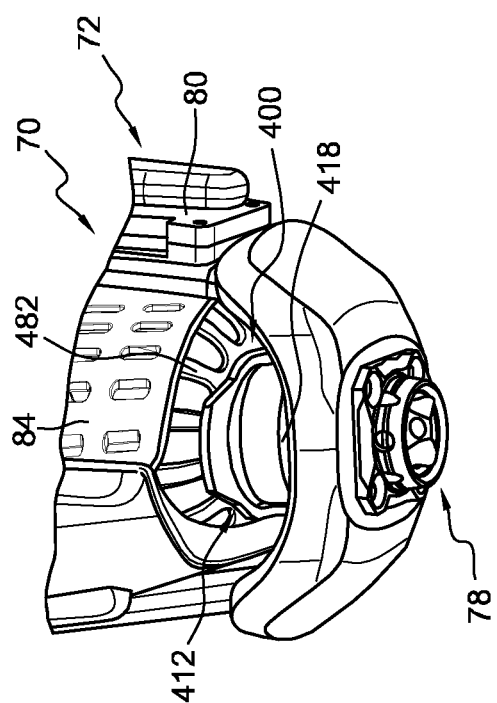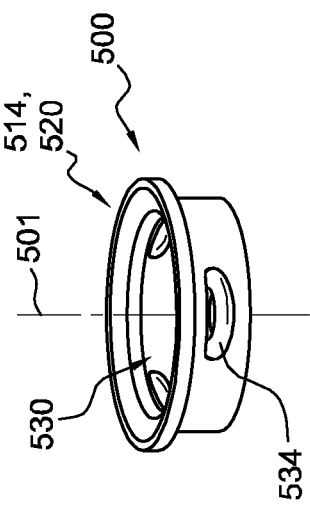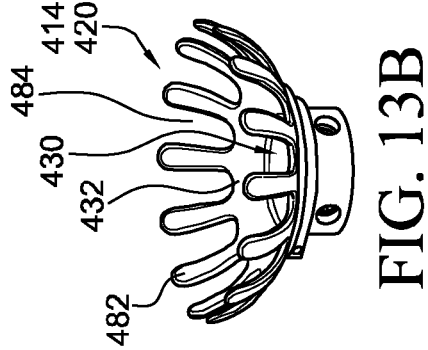
FIG. 15
FIG. 16
FIG. 17
FIG. 13A
FIG. 14
FIG. 13B

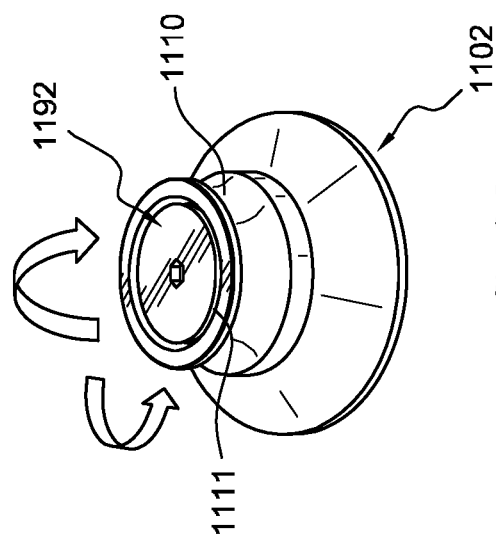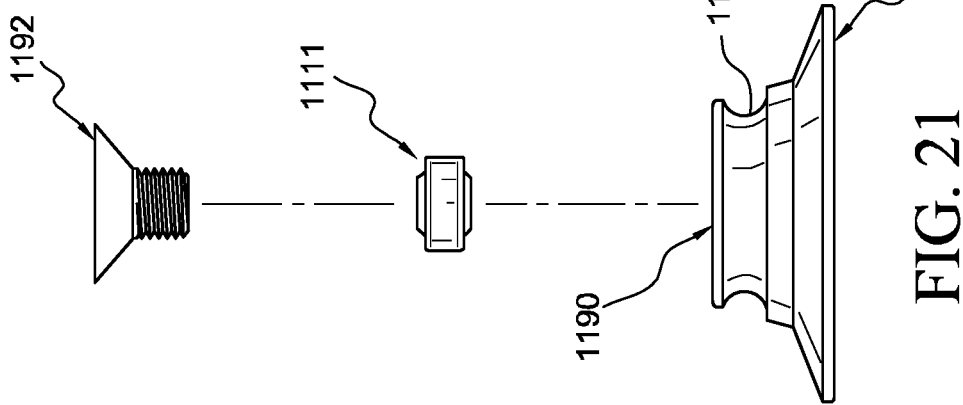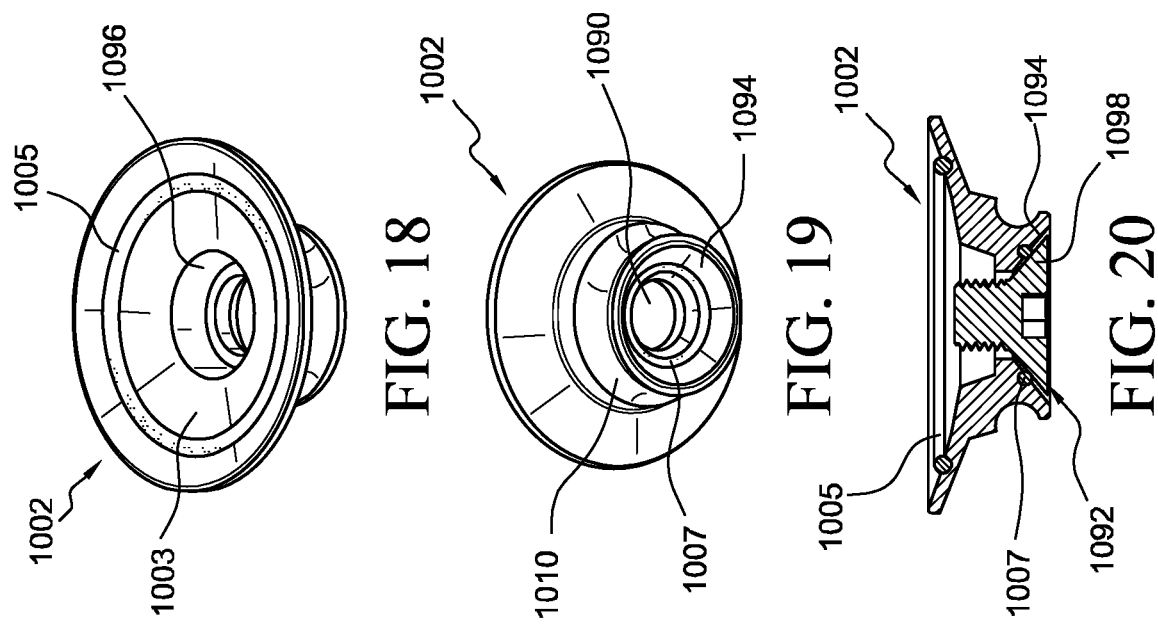

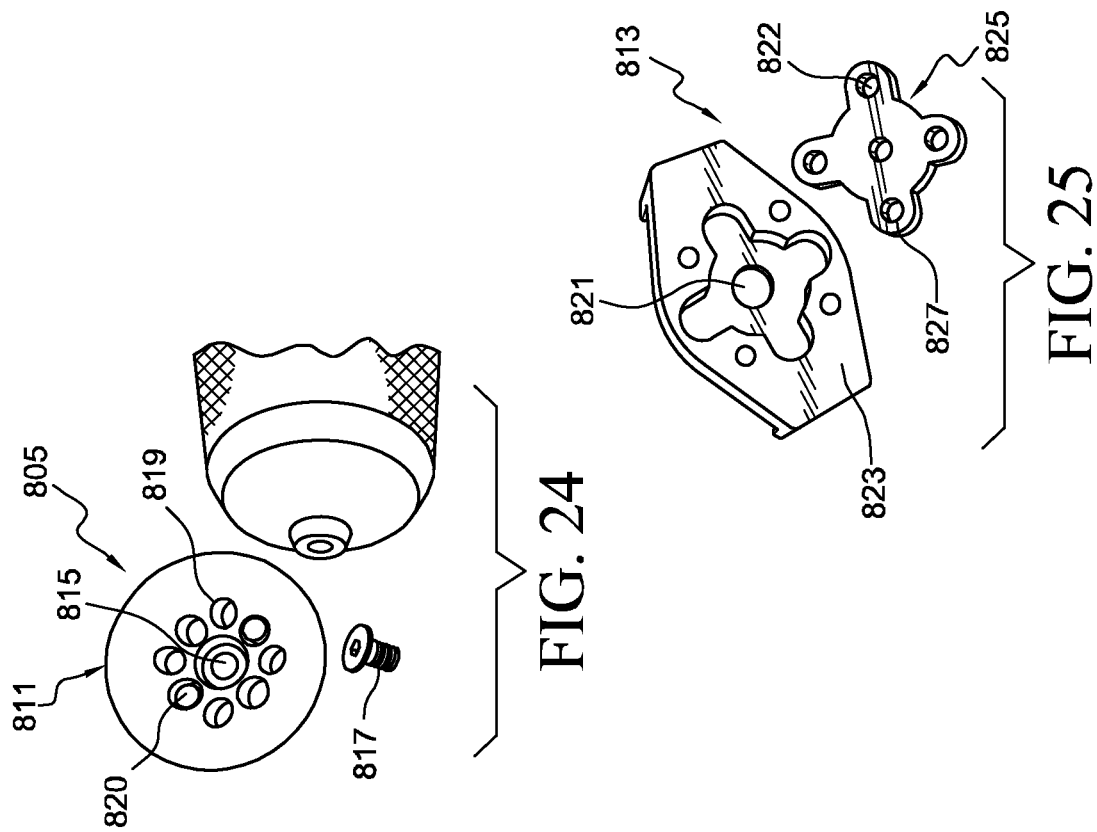
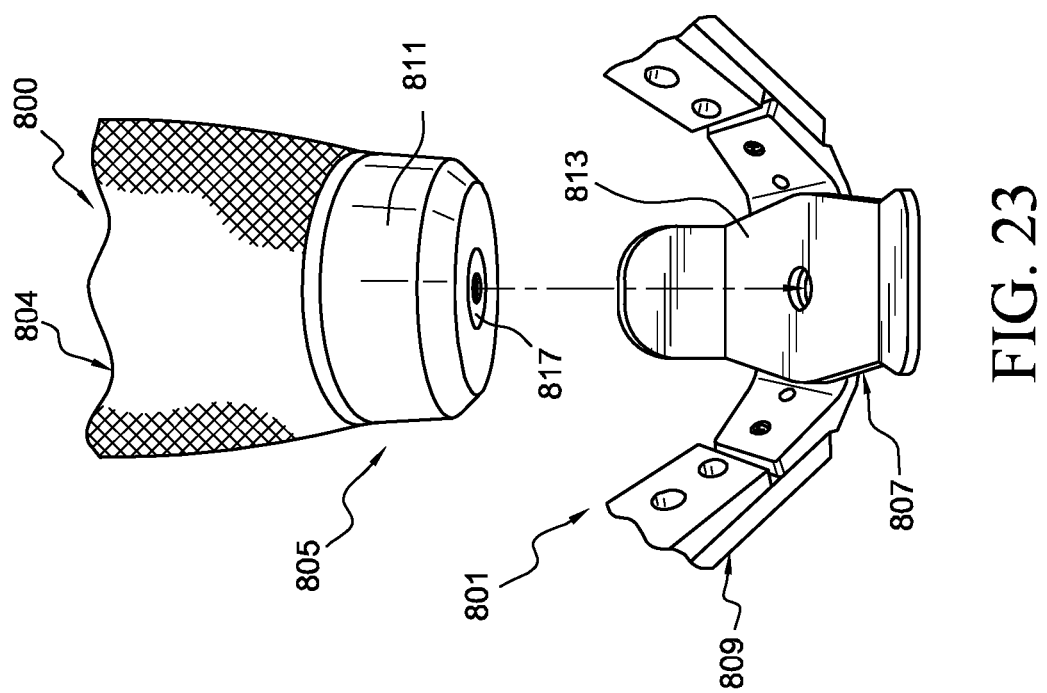

PROSTHETIC ATTACHMENT SYSTEM

TECHNICAL FIELD

The disclosure relates to attachment systems for a prosthetic socket.

BACKGROUND

A typical prosthetic leg and foot includes a socket, pylon, and foot. A socket is commonly referred to as the portion of a prosthesis that fits around and envelops a residual limb or stump, and to which prosthetic components, such as a foot, are attached. The socket must fit closely to the residual limb to provide a firm connection and support, but must also be sufficiently loose to allow for circulation. In combination with proper fitting, the socket must transfer loads from the residual limb to the ground in a comfortable manner.

To increase comfort, it may be provided that a prosthetic liner is arranged between the socket and the residual limb. In general, the prosthetic liner includes an elastomeric body having a closed distal end and an open proximal end that is pulled over the residual limb in the manner of a sock. The prosthetic liner adheres to the residual limb surface and generates the connection between the residual limb and the socket.

For attaching the prosthetic liner to the socket, locking pins may be provided at the distal end of the prosthetic liner and a corresponding attachment lock may be provided at the distal end of the socket, which locks the prosthetic liner to the socket after insertion into the socket. The attachment of the prosthetic liner to the socket can be released via an unlocking mechanism.

A further possibility for attaching a socket to a residual limb resides in what is known as vacuum suspension, in which the socket seals airtight against the prosthetic liner and air present in the space between the prosthetic liner and the socket is pulled or forced out. This creates a suction tending to retain the prosthetic liner within the socket.

These socket attachment systems have their drawbacks. For instance, vacuum suspension systems can only be used with sockets that are airtight. In addition, the strength and reliability of the connection between the prosthetic liner and the socket can be compromised and/or broken due to irregular loading of the socket by the user, excessive relative movement between the prosthetic liner and the socket, perspiration, and/or other factors.

Locking pin-type systems also tend to incorrectly lock if a user does not fully insert the locking pin into the lock. This can result in failure of the lock and/or significant injury to the user. In addition, too much free play between the locking pin and the lock can result in a slack connection, such that the residual limb undesirably moves up and down within the socket when the user is walking (known as pistoning). This can also create noise, which can be of great annoyance and embarrassment to the user. The free play may also lead to premature wear of the pin and lock components which can ultimately result in failure of the lock. Locking pin-type systems are also known to make optimum orientation of the residual limb/liner in the socket difficult. Further, the attachment lock is formed into the socket during manufacture. The orientation must therefore be selected before fitting is performed and thus is not tailored towards a specific patient.

There is thus a need for a prosthetic attachment system that provides a more reliable and secure connection between a residual limb and a prosthetic socket. There is also a need for a prosthetic attachment system that makes donning and doffing a prosthetic socket easier and more intuitive, and which minimizes pistoning and incorrect locking of the system.

SUMMARY

The disclosure describes various embodiments of a prosthetic attachment system providing a construction and design that facilitates a more reliable and secure connection between a residual limb and a prosthetic socket.

According to a variation, a prosthetic attachment system includes an insert arranged for connection to a distal end of a prosthetic liner and an attachment unit arranged for connection to a base distal end of a socket. The insert includes an outer radial surface defining a circumferential locking groove. The attachment unit comprises a body carrying a plurality of locking elements and defining a central opening for selectively receiving the insert.

The locking elements are distributed circumferentially about an axis of the body and are radially repositionable relative to the axis. A release mechanism is slidably positioned on an outer surface of the body. The release mechanism is repositionable on the body to move the prosthetic attachment system between a locked configuration in which the locking elements move radially inward relative to the axis of the body to lock the insert in the body and an unlocked configuration in which the locking elements move radially outward relative to the axis to release the insert from the body.

In the locked configuration, the locking elements engage the circumferential locking groove on the insert in a close-fitting manner and at multiple points distributed circumferentially about the axis of the body, enhancing a strength and/or a stiffness of the attachment between the insert and the attachment unit. As such, axial movement and tilting between the insert and attachment unit are prevented or substantially limited. This advantageously helps reduce the likelihood of undesirable free play and/or slack commonly found in locking pin-type systems which can result in user discomfort and/or failure of the prosthetic socket system. According to a variation, the attachment between the insert and the attachment unit is arranged to provide a selected amount of free play between the insert and the attachment unit. For instance, the attachment between the insert and the attachment unit can be arranged to prevent or substantially prevent relative axial movement but allow an amount of rotation or tilting between the insert and the attachment unit.

The secure attachment between the insert and the attachment unit also reduces noise generated at the attachment between the prosthetic liner and the socket during gait, which can be of great annoyance and embarrassment to the user. Moreover, the attachment between the residual limb and the socket can be automatically effectuated when the insert is inserted into the body, reducing the likelihood of user error and significant injury to the user.

According to a variation, when the user wishes to release the insert from the attachment unit, the user can push or pull the release mechanism downward along the outer surface of the body. This generally aligns an inclined surface on the release mechanism with the locking elements, providing a clearance or space for the locking elements to move radially outward. Simultaneously or nearly simultaneously, stored energy in the attachment unit can force a stop member below the body upwardly, driving the locking elements radially outward into engagement with the inclined surface of the release mechanism. The engagement between the inclined surface of the release mechanism and the locking elements may maintain the prosthetic attachment system in the locked position.

According to a variation, the attachment unit includes one or more alignment features for guiding the insert into the attachment unit, advantageously making donning of a socket easier by helping to properly align the insert with the attachment unit. Moreover, the insert and central opening can be relatively large compared to a conventional locking pin and corresponding pin hole, which facilitates alignment of the prosthetic liner within the socket. This is particularly advantageous for elderly users having limited dexterity.

The prosthetic attachment system of the present disclosure thus beneficially facilitates donning and doffing of a prosthetic socket as good hand dexterity and/or strength are not required to operate the attachment system. Rather, a prosthetic liner can be automatically locked in the socket and easily released from the socket with a simple manipulation of the release mechanism. In addition, the prosthetic attachment system can assist a user with placement of the prosthetic liner in the socket. Moreover, the prosthetic attachment system can be used with both conventional airtight sockets and adjustable sockets that are not airtight, increasing its versatility.

BRIEF DESCRIPTION OF THE DRAWINGS

These and other features, aspects, and advantages of the present disclosure will become better understood regarding the following description, appended claims, and accompanying drawings.

FIG. 3 is a side view of a prosthetic liner and a prosthetic attachment system according to an embodiment.

FIG. 4 is a cross section of the attachment system of FIG. 3 in an unlocked configuration.

FIG. 5 is a cross section of the attachment system of FIG. 3 in a locked configuration.

FIG. 6 is a side perspective view of a prosthetic socket system according to another embodiment.

FIG. 7 is a perspective view of the attachment unit of FIG. 6.

FIG. 8 is a partial cross section of the prosthetic socket system of FIG. 6.

FIG. 9a is a side perspective view of a prosthetic socket system including a prosthetic attachment system in a locked configuration according to another embodiment.

FIG. 9b is a side perspective view of the prosthetic socket system of FIG. 9a showing the attachment system in an unlocked configuration.

FIG. 10 is a cross section of the attachment system of FIG. 9a.

FIG. 11a is a side view of the attachment system of FIG. 9a in a locked configuration.

FIG. 11b is a side view of the attachment system of FIG. 9a in an unlocked configuration.

FIG. 12a is a side perspective view of a prosthetic socket system according to another embodiment.

FIG. 12b is a partial cross section of the attachment system in FIG. 12a.

FIG. 13a is a bottom perspective view of a prosthetic socket system according to another embodiment.

FIG. 13b is a top perspective view of the lock body of FIG. 13a.

FIG. 14 is a side perspective view of a lock body according to another embodiment.

FIG. 15 is a cross section of a prosthetic socket system according to another embodiment.

FIG. 16 is a bottom perspective view of an attachment system according to another embodiment.

FIG. 17 is a cross section of the insert of FIG. 16.

FIG. 18 is a top perspective view of an attachment system according to another embodiment.

FIG. 19 is a bottom perspective view of the insert of FIG. 18.

FIG. 20 is a cross section of the insert of FIG. 18.

FIG. 21 is a side exploded view of an attachment system according to another embodiment.

FIG. 22 is a bottom perspective view of the insert of FIG. 21.

FIG. 23 is a side perspective view of a prosthetic socket system according to another embodiment.

FIG. 24 is a partial exploded view of the attachment system of FIG. 23.

FIG. 25 is another partial exploded view of the attachment system of FIG. 23.

DETAILED DESCRIPTION OF VARIOUS EMBODIMENTS

Figure 2:
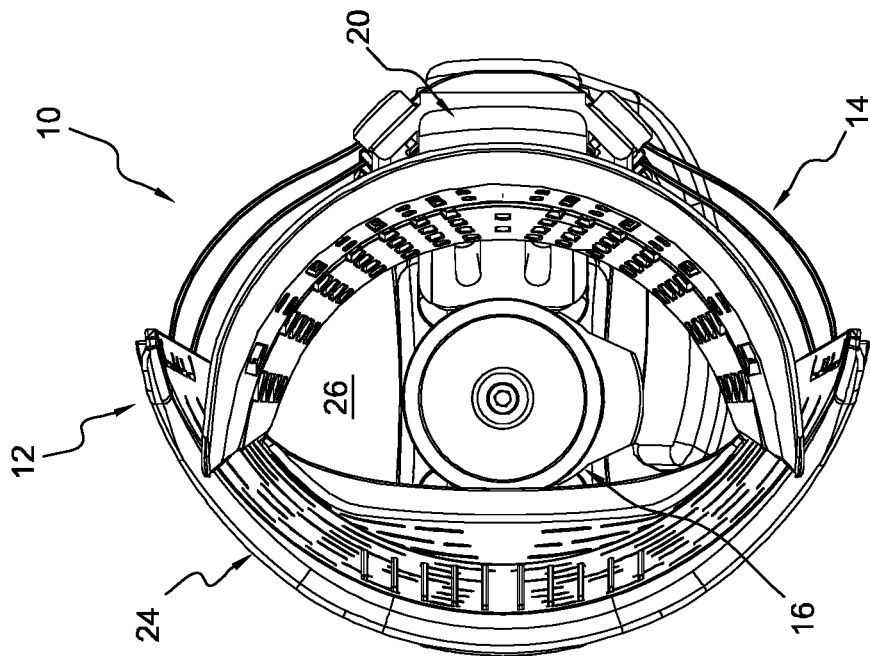
FIG. 2 is a top view of the prosthetic socket system of FIG. 1.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the specific embodiments disclosed, but on the contrary, the intention covers all modifications, alternative constructions, combinations, and equivalents falling within the spirit and scope of the disclosure.

It will be understood that unless a term is expressly defined in this application to possess a described meaning, there is no intent to limit the meaning of such term, either expressly or indirectly, beyond its plain or ordinary meaning. Any element in a claim that does not explicitly state "means for" performing a specified function, or "step for" performing a specific function is not to be interpreted as a "means" or "step" clause as specified in 35 U.S.C. § 112(f).

Figure 1:
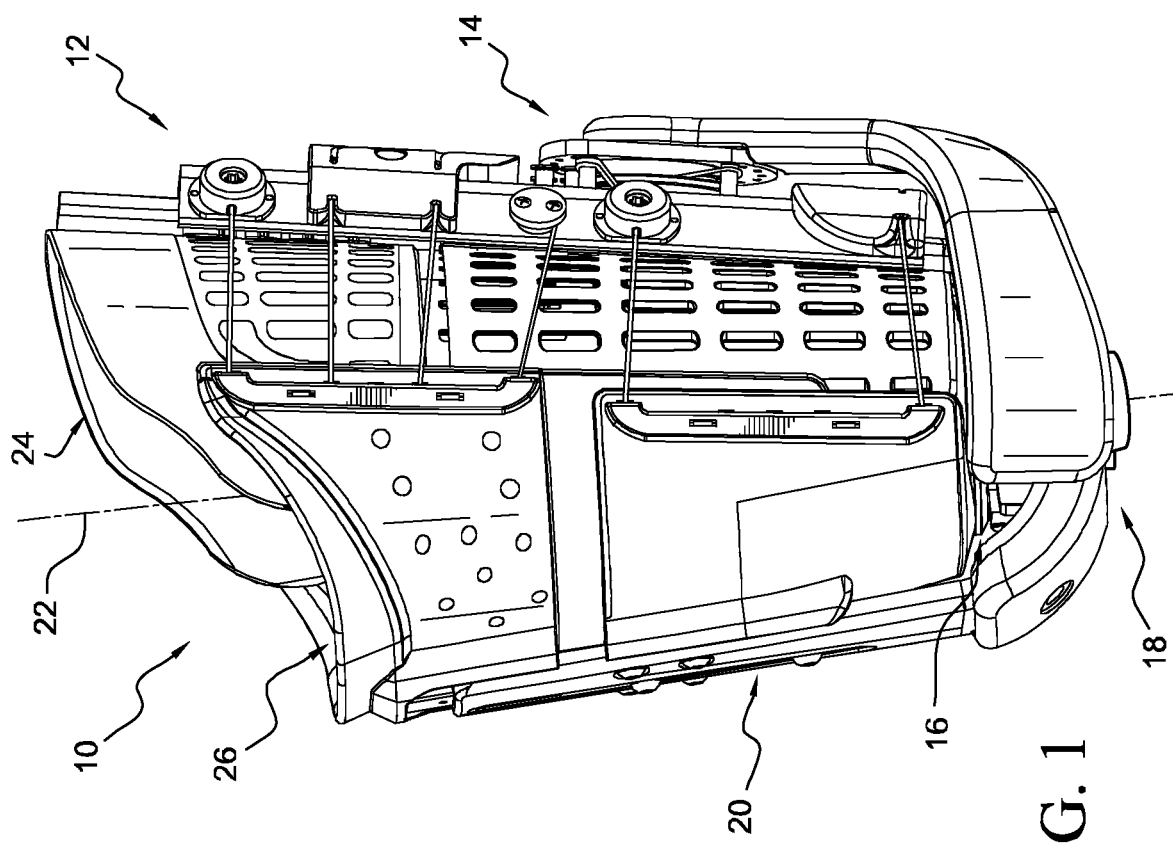
FIG. 1 is a side view of a prosthetic socket system according to an embodiment.

FIGS. 1 and 2 illustrate a prosthetic socket system 10 according an embodiment including a socket 12, a prosthetic liner, and a prosthetic attachment system 16 arranged to quickly and securely suspend the socket 12 on a residual limb donning the prosthetic liner. The attachment system 16 can include an insert arranged for connection to a distal end of the prosthetic liner and an attachment unit arranged for connection to a base or distal end of the socket 12. The insert can include an outer radial surface defining a circumferential locking groove and the attachment unit can include a body carrying a plurality of locking elements and defining a central opening for selectively receiving the insert.

The locking elements of the body of the attachment unit are distributed circumferentially about a longitudinal axis 22 of the prosthetic socket system 10 and are radially repositionable relative to the longitudinal axis 22. In an embodiment, the longitudinal axis 22 generally corresponds to an axis of the body. A release mechanism is slidably positioned on an outer surface of the body. The release mechanism is repositionable on the body to move the attachment system 16 between a locked configuration in which the locking elements move or shift radially inward relative to the longitudinal axis 22, locking the insert in the body and an unlocked configuration in which the locking elements move or shift radially outward relative to the longitudinal axis 22, releasing the insert from the body.

In the locked configuration, the locking elements of the body of the attachment unit selectively engage the locking groove on the insert in a close-fitting manner and at multiple points circumferentially distributed about the longitudinal axis 22, enhancing a strength and/or a stiffness of the attachment between the insert and the attachment unit. As such, axial movement and tilting between the insert and body is substantially limited. This advantageously helps reduce the likelihood of undesirable free play and/or slack in the attachment system 16 which can result in user discomfort and/or failure of the prosthetic socket system 10. According to a variation, the attachment between the insert and the attachment unit is arranged to provide a selected amount of free play between the insert and the attachment unit. For instance, the attachment between the insert and the attachment unit can be arranged to prevent or substantially prevent relative axial movement but allow an amount of rotation or tilting between the insert and the attachment unit.

It also reduces noise generated by the attachment system 16, which can be of great annoyance and embarrassment to the user. Moreover, the attachment system 16 can automatically lock the insert in the body when it is received therein, reducing the likelihood of user error and significant injury to the user.

When a user wants to release the insert from the attachment unit, the user can push or pull the release mechanism downward along the outer surface of the body of the attachment unit. This generally aligns an inclined surface on the release mechanism with the locking elements, providing a clearance or space for the locking elements to move radially outward. Simultaneously or nearly simultaneously, stored energy in the attachment unit can drive the locking elements radially inward into engagement with the inclined surface of the release mechanism. The engagement between the inclined surface of the release mechanism and the locking elements may maintain the attachment system in the locked position.

It will be appreciated that the attachment unit can include one or more alignment features for guiding the insert into the attachment unit, advantageously making donning of the socket 12 easier by helping to properly align the insert and prosthetic liner with the attachment unit. It also helps to forgive poor alignment of the prosthetic liner within the socket 12. Moreover, the insert and central opening can be relatively large compared to a conventional locking pin and corresponding pin hole, which facilitates alignment of the prosthetic liner 14 within the socket 12. This is particularly advantageous for elderly users having limited dexterity.

Referring now the prosthetic socket system 10 generally, the socket 12 can be any suitable type of socket. For instance, the socket 12 can comprise a conventional socket that is rigid and has a general uniform shape which receives a portion of a residual limb. In the illustrated embodiment, the socket 12 comprises an adjustable socket including a base 18, a plurality of longitudinal supports 20 connected to the base 18 and distributed about the longitudinal axis 22, and a plurality of shell components 24 connected to the longitudinal supports 20. The shell components 24 collectively form a socket wall defining a receiving volume 26 adapted to receive a residual limb. The base 18 is arranged to provide support for a distal end of the residual limb and can include at least a portion of the attachment system 16 for fixing or securing the residual limb or a liner to the base 18. The longitudinal supports 20 are shown comprising medial and lateral supports but can be in any suitable configuration.

The socket 12 is radially adjustable between an open configuration and a closed configuration. In the open configuration, at least some of the longitudinal supports 20 and/or shell components 24 are free to move or are forced radially outward relative to the longitudinal axis 22 of the prosthetic socket system 10, increasing the receiving volume 26 or increasing a circumference of the socket 12. This effectively loosens the fit of the prosthetic socket 12 on a residual limb inserted in the receiving volume 26, or decreases the loading on the residual limb from the socket wall.

In the closed configuration, at least some of the longitudinal supports 20 and/or the shell components 24 are moved or forced radially inward relative to the open configuration, decreasing the receiving volume 26 or decreasing the circumference of the socket 12. It will be appreciated that movement of any portion of a longitudinal support 20 or a shell component 24 can move the socket 12 between the expanded and closed configurations.

A tensioning system 14 is arranged to selectively secure a residual limb within the receiving volume 26 by moving the socket 12 between the open/expanded and closed configurations. Other examples and additional details of suitable prosthetic sockets are included in U.S. Pat. Nos. 8,795,385, 9,248,033, 9,050,202, and U.S. patent application Ser. Nos. 14/704,572, 15/151,204, 15/888,403, and 15/888,288, each of which is incorporated by reference in its entirety.

With reference to FIGS. 3-20, various embodiments of the attachment system 16 are illustrated. For instance, FIGS. 3-5 illustrate a prosthetic attachment system 100 according to an embodiment including an insert 102 and an attachment unit 112. As shown in FIG. 3, the insert 102 is arranged to be connected to a prosthetic liner 104. The prosthetic liner 104 can include a flexible and elongate liner body 106 formed from an elastomeric material. The liner body 106 defines an inner surface and an outer surface forming a liner profile between a closed distal end 108 and an open proximal end. It will be appreciated that the prosthetic liner 104 can be any suitable type of prosthetic liner.

The insert 102 can be connected to the closed distal end 108 in any suitable manner. For instance, the insert 102 can be threadedly attached to the closed distal end 108 of the prosthetic liner 104. In other embodiments, the insert 102 can be integral to the prosthetic liner 104 or attached to the closed distal end 108 of the prosthetic liner 104 via at least one fastener.

The insert 102 includes an outer radial surface defining a locking groove 110 extending circumferentially about the insert 102 and an upper surface arranged for connection to the closed distal end 108 of the prosthetic liner 104. The locking groove 110 can have any suitable cross-sectional shape but is shown having a concave cross-section. The insert 102 can be made of any suitable material. The material selection can depend on desired function. The insert 102 may include a stiff elastomeric material such as a stiff silicone, enhancing the durability and/or stability of the insert 102. The insert 102 can include a stiff plastic material, a metal material, or any other suitable material.

The attachment unit 112 can be integral to a base or distal end of a socket or attached to the base or distal end of the socket. For instance, the attachment unit 112 can be connected to the base via at least one fastener. This can allow for existing sockets to be easily retrofitted with the attachment unit 112.

The insert 102 can be automatically secured in or against the attachment unit 112 when the prosthetic liner 104 is positioned in the socket. For instance, the attachment unit 112 can be spring loaded to automatically lock the prosthetic liner 104 and the base of the socket together when the insert 102 is inserted in the attachment unit 112, achieving prosthetic suspension. As described above, the attachment system 100 advantageously facilitates donning and doffing of the socket, and creates a secure attachment between the prosthetic liner 104 and a socket. The attachment unit 112 includes a body 114 and a release mechanism 116 comprising a collar movable positioned on the body 114. The body 114 can include a support body 118, a lock body 120, and a stop member 122. The body 114 can include a stiff plastic material, a metal material, or any other suitable material.

As best seen in FIGS. 4 and 5, the support body 118 includes an upper surface that can be in contact with and is arranged to cooperate with a bottom surface of the lock body 120 and an outer peripheral surface that can be in contact with and is arranged to cooperate with an inner surface 138 of the release mechanism 116. The support body 118 defines an opening 124 having a generally closed bottom arranged for selectively receiving the stop member 122. It will be appreciated that in other embodiments the support body 118 can be integrated with a base of a socket.

At least one resilient member 126 is disposed between the support body 118 and the stop member 122. The at least one resilient member 126 can comprise a plurality of spring members 128 circumferentially distributed about the axis 25. The spring members 128 collectively bias the stop member 122 away from the bottom of the support body 118. The support body 118 can define a lower radial flange 130 extending under the release mechanism 116.

The lock body 120 is supported on and/or connected to the support body 118. The lock body 120 may be connected to the support body 118 in any suitable manner such as via one or more fasteners. While the lock body 120 is shown separate from the support body 118, in other embodiments, the support body 118 and the lock body 120 may comprise a single body or member.

A central opening 130 is defined in the body 114 that is sized and configured to receive the insert 102. For instance, the lock body 120 can define the central opening 130 and include an annular flange 132 surrounding the central opening 130 and extending axially upward and radially away from a top of the central opening 130 as shown in FIG. 4. The annular flange 132 can funnel or guide the insert 102 into the central opening 130. This advantageously makes donning of the socket easier by helping to align the insert 102 with the attachment unit 112. This also helps forgive poor alignment of the prosthetic liner 104 within the socket. Moreover, the insert 102 and central opening 130 can be relatively large compared to a conventional locking pin and corresponding pin hole, which facilitates alignment of the prosthetic liner 104 within a socket. This is particularly advantageous for elderly users having limited dexterity, as the user does not have to "thread the needle," so to speak, increasing risk of incorrect attachment and injury, but rather the user is provided with an intuitive and forgiving attachment procedure.

A plurality of locking elements 134 are carried by the lock body 120. The locking elements 134 can be mounted or otherwise attached to the lock body 120 in any suitable manner. For instance, the locking elements 134 can be mounted within holes 136 formed in the lock body 120 arranged for receiving the locking elements 134. The holes 136 can be sized and shaped to generally correspond to the locking elements 134.

The locking elements 134 are radially repositionable relative to an axis 25 of the body 114 such that the locking elements 134 can at least in part move into and out of the central opening 130 of the body 114. The locking elements 134 can be made of any suitable rigid material. For instance, the locking elements 134 may be formed of steel. In other embodiments, the locking elements 134 may be formed of ceramic material or plastic material, reducing the overall weight and cost of the attachment unit 112. The locking elements 134 are shown comprising ball bearing elements but can be any suitable locking elements such as, for example, ring segments or block elements.

The release mechanism 116 is slidably positioned on the body 114 such that the release mechanism 116 is axially repositionable along an outer surface of the body 114. The release mechanism 116 includes an inner surface 138 defining a lower interior wall 140 generally corresponding to outer surfaces of the support body 118 and/or the lock body 120, and an inclined surface 142 extending from the lower interior wall 140. The inclined surface 142 extends upward and radially outward from the lower interior wall 140. The inclined surface 142 can be an angled and/or conical surface extending around the central opening 130 of the lock body 120.

The lower interior wall 140 can generally correspond to an outer periphery of the support body 118 comprising a pair of parallel sides connected by a pair of convex or semi-circular sides at opposite ends. This arrangement beneficially helps prevent relative rotation between the release mechanism 116 and at least the support body 118. The lower interior wall 140 of the release mechanism 116 can comprise a generally upright surface. According to a variation, a top surface of the release mechanism 116 can define a shoulder 144 generally corresponding to the bottom of the annular flange 132 on the lock body 120. Relative axial movement between the release mechanism 116 and the lock body 120 can be limited by engagement of the shoulder 144 with the bottom of the annular flange 132.

Axial movement of the release mechanism 116 on the body 114 moves the attachment system 100 between an unlocked configuration (shown in FIG. 4) and a locked configuration (shown in FIG. 5) in which the locking elements 134 lock the insert 102 in the attachment unit 112.

In the unlocked position, the at least one resilient member 126 bias the stop member 122 upwardly away from the support body 118 and into the central opening 130 of the lock body 120 such that an outer surface 146 of the stop member 122 contacts and drives the locking elements 134 radially outward, which, in turn, engage the inclined surface 142 on the release mechanism 116. This engagement between the locking elements 134 and the inclined surface 142 holds or maintains the release mechanism 116 in a first or down position and the attachment system 100 in the unlocked configuration.

Optionally, the release mechanism 116 can compress one or more secondary spring members 148 (shown in FIG. 3) disposed between the release mechanism 116 and the support body 118 when the release mechanism 116 is in the down position. For instance, the one or more secondary spring members 148 can be positioned between a lower radial flange 150 (shown in FIG. 3) of the support body 118 and a lower surface of the release mechanism 116. The one or more secondary spring members 148 can comprise a plurality of secondary spring members or a single secondary spring member surrounding the support body 118.

When a user positions the prosthetic liner 104 into the socket, the insert 102 can be guided into the central opening 130 of the lock body 120 by the annular flange 132, reducing the likelihood of incorrect liner alignment and improving ease of use. Moreover, the insert 102 and the central opening 130 are relatively large compared to a conventional locking pin and corresponding pin hole, which, in turn, facilitates simpler and easier alignment of the prosthetic liner 104 and donning of the socket. As the insert 102 moves through the central opening 130 of the lock body 120, the bottom surface of the insert 102 engages and pushes down on the stop member 122 against the force of the at least one resilient member 126, which, in turn, permits the locking elements 134 to move radially inward and the secondary spring members 148 to force the release mechanism 116 upward along the outer surface of the body 114 toward a second or up position.

As the release mechanism 116 moves upwardly along the outer surface of the body 114, the lower interior wall 140 on the release mechanism 116 contacts and drives the locking elements 134 radially inward and into the locking groove 110 of the insert 102. This moves the attachment system 100 into the locked configuration, securely locking the insert 102 in the attachment unit 112 and the prosthetic liner 104 in the socket. The attachment system 100 thus automatically attaches the prosthetic liner 104 to the socket when the insert 102 is inserted into the body 114, reducing the likelihood of user error and significant injury to the user. This is advantageous because conventional locking pin-type systems tend to incorrectly lock if a user does not fully insert the locking pin into the lock, leading to potential damage or injury if the socket and liner detach during use.

In the locked configuration, the locking elements 134 engage the locking groove 110 in a close-fitting manner and at multiple points distributed circumferentially about the axis 25 of the body 114, enhancing a strength and/or a stiffness of the attachment between the insert 102 and the attachment unit 112. For instance, the locking elements 134 can create between about 2 and about 6 (e.g., about 4) physical connections between the body 114 and the insert 102 about the circumference of the insert 102. As such, axial movement and/or tilting between the insert 102 and the attachment unit 112 are substantially limited. This advantageously helps reduce the likelihood of undesirable free play and/or slack commonly found in locking pin-type systems which can result in user discomfort and/or failure of the prosthetic socket system. It also makes the prosthetic suspension of a socket on a residual limb more reliable and less prone to failure due to movement, loading, and perspiration when compared to conventional vacuum suspension systems. Further, the attachment system 100 can be safely and conveniently used with a socket that is not airtight.

The stability of the attachment between the insert 102 and the attachment unit 112 also reduces noise generated at the attachment between the prosthetic liner and the socket during gait, which can be of great annoyance and embarrassment to the user. According to a variation, the attachment between the insert 102 and the attachment unit 112 is arranged to provide a selected amount of free play between the insert 102 and the attachment unit 112. For instance, the attachment between the insert 102 and the attachment unit 112 can be arranged to prevent or substantially prevent relative axial movement but allow an amount of rotation or tilting between the insert 102 and the attachment unit 112.

When the user wants to release the insert 102 and/or the prosthetic liner 104 from the attachment unit 112, the user can move the release mechanism 116 downward on the body 114 against the force of the secondary spring members 148. In an embodiment, the user can push or pull the release mechanism 116 downward along the outer surface of the body 114. This generally aligns the inclined surface 142 of the inner surface 138 of the release mechanism 116 with the locking elements 134, providing a clearance or space for the locking elements 134 to move radially outward.

Simultaneously or nearly simultaneously, stored energy in the at least one resilient member 126 forces the stop member 122 upwardly, driving the locking elements 134 radially outward into engagement with the inclined surface 142 of the release mechanism 116 and out of engagement with the locking groove 110. These biased engagements prevent the release mechanism 116 from undesirably moving back toward the up position. The at least one resilient member 126 also allows a user to move the attachment system 100 toward the unlocked configuration with less strength and/or dexterity because the stored energy in the at least one resilient member 126 assists the user in moving the release mechanism 116 toward the down position, improving ease of use.

According to a variation, the attachment unit 112 and/or insert 102 can be arranged to provide an indicator (e.g., a click or vibration) when the attachment system 100 has moved to the locked configuration, helping a user determine when a socket is safely suspended on the residual limb. This advantageously improves ease of use and helps reduce the likelihood of injury to a user.

The attachment unit 112 and/or insert 102 may also be arranged to provide a unique indicator (e.g., a double click) when the attachment system 100 has moved to the unlocked configuration, signaling to a user that the socket is ready to be doffed. This advantageously improves ease of use and helps reduce the likelihood of over-exertion by the user.

The attachment system 100 can include at least one manipulation feature 152 arranged to help a user move the attachment system 100 between the locked configuration and the unlocked configuration. For instance, the at least one manipulation feature 152 can comprise a circumferential protruding part or ridge 154 on the release mechanism 116. The ridge 154 is sized to assist the user in moving the attachment system 100 toward the unlocked configuration.

The attachment system 100 thus beneficially facilitates donning and doffing of a prosthetic socket as good hand dexterity and muscular strength are not required to operate the attachment system 100. Rather, the prosthetic liner 104 can be automatically locked in the socket and easily released from the prosthetic liner 104 with a simple manipulation of the release mechanism 116. In addition, the attachment system 100 can assist a user with placement of the prosthetic liner 104 in the socket, improving ease of use. Moreover, the attachment system 100 can be used with both conventional airtight sockets and adjustable sockets that are not airtight, increasing its versatility.

It will be appreciated that while the release mechanism 116 is shown as a collar, in other embodiments, it can comprise any suitable type of release mechanism. For instance, the release mechanism 116 can comprise one or more buttons, levers, cam mechanisms, handles, ramp members, combinations thereof, or any other suitable release mechanism.

FIGS. 6-8 illustrate a prosthetic socket system 30 according to another embodiment. It will be appreciated that the prosthetic socket system 30 may be similar in many respects to the prosthetic socket system 10 and may incorporate any feature described herein.

The prosthetic socket system 30 includes a socket 32, a prosthetic liner 204, and a prosthetic attachment system 200 arranged to quickly and securely suspend the socket 32 on a residual limb donning the prosthetic liner 204. The socket 32 comprises an adjustable socket including a base 38, and a plurality of longitudinal supports 40 connected to the base 38. The longitudinal supports 40 are distributed about a longitudinal axis 42 of the prosthetic socket system 30. For ease of reference, the socket 32 is shown without shell components attachable to the longitudinal supports 40.

The attachment system 200 includes an insert 202 arranged for connection to the prosthetic liner 204 and an attachment unit 212 arranged for connection to the base 38 of the socket 30. The attachment unit 212 includes a release mechanism 216 arranged to help move the attachment system 200 between a locked configuration in which the insert 202 is locked in the attachment unit 212, and an unlocked configuration in which the insert 202 is released from the attachment unit 212. Similar to the attachment system 100, the attachment system 200 is arranged to automatically move to the locked configuration when the insert 202 is inserted in the attachment unit 212.

The attachment unit 212 includes a body 214 having a support body 218, a lock body 220, and a stop member 222. The release mechanism 216 comprises a collar movably positioned on the body 214. The support body 218 includes a central portion 256 defining an opening 224 having a generally closed bottom arranged for selectively receiving the stop member 222, a base section 258 below the central portion 256, and a plurality of wall sections 260 extending upwardly from the base section 258.

A radial space or gap 262 is formed between the central portion 256 and the wall sections 260 to accommodate axial movement of the release mechanism 216 on the body 214 between the wall sections 260 and the central portion 256. This advantageously helps reduce the overall size and profile of the attachment system 200 because the main outer diameter of the release mechanism 216 is generally smaller than the outer diameter of the support body 218. One or more circumferential gaps are formed between adjacent ones of the wall sections 260 to accommodate a manipulation feature of the release mechanism 216 described below when the attachment system 200 is in an unlocked configuration.

Referring to FIG. 8, at least one resilient member 226 is disposed between the support body 218 and the stop member 222. The at least one resilient member 226 comprises a single central spring member 228 positioned within the opening 224 of the support body 218. The central spring member 228 is arranged to bias the stop member 222 away from the bottom of the support body 218 or away from the base 38. The lock body 220 carries a plurality of locking elements 234 and is supported by and/or attached to the support body 218. The locking elements 234 are radially repositionable relative to the longitudinal axis 42. In an embodiment, the longitudinal axis 42 generally corresponds to an axis of the body 214.

The release mechanism 216 is slidably positioned on an outer surface of the body 214 such that the release mechanism 216 can be axially or vertically repositioned on the body 214 to radially reposition the locking elements 234 relative to the longitudinal axis 42, which, in turn, moves the attachment system 200 between the locked configuration and the unlocked configuration.

The release mechanism 216 defines an inner surface 238 having a lower interior wall 240 and an inclined surface 242 extending upwardly and radially outwardly from the lower interior wall 240. The lower interior wall 240 can generally correspond to the outer surface of the lock body 220 and the outer surface of the central portion 256. For instance, the lower interior wall 240 can form a periphery having a pair of parallel sides connected by a pair of convex or semicircular sides at opposite ends. This arrangement beneficially helps prevent relative rotation between the release mechanism 216 and the body 214.

The attachment system 200 can include at least one manipulation feature 252 (shown in FIGS. 6 and 7) arranged to help a user move the attachment system 200 between the locked configuration and the unlocked configuration. The at least one manipulation feature 252 can comprise a button part 254 (shown in FIGS. 6 and 7) on the release mechanism 216 sized and configured to assist a user in moving the attachment system 200 toward the unlocked configuration.

In the unlocked configuration, the central spring member 228 biases the stop member 222 upwardly within a central opening 230 of the lock body 220 such that an outer surface of the stop member 222 contacts and drives the locking elements 234 radially outward relative to the longitudinal axis 42, which, in turn, engage the inclined surface 242 of the release mechanism 216.

This engagement between the locking elements 234 and the inclined surface 242 of the release mechanism 216 holds or maintains the release mechanism 216 in a first or down position on the body 214. According to a variation, one or more secondary spring members 248 are positioned between the base section 258 of the support body 218 and the release mechanism 216. The one or more secondary spring members 248 can be compressed when the attachment system 200 is in the unlocked position and can comprise a plurality of secondary spring members or a single secondary spring member surrounding the support body 218.

When the insert 202 is inserted into the central opening 230 of the lock body 220, the insert 202 exerts a downward force on the stop member 222 against the force of the central spring member 228, which, in turn, permits the locking elements 234 to move radially inward and the one or more secondary spring members 248 to force or drive the release mechanism 216 upward along the outer surface of the body 214 from a first position toward a second or up position.

As the release mechanism 216 moves upwardly, the lower interior wall 240 of the release mechanism 216 contacts and drives the locking elements 234 radially inward and into the locking groove 210 of the insert 202. This moves the attachment system 200 to the locked configuration, locking or securing the insert 202 in the attachment unit 212. In the locked configuration, the locking elements 234 engage the locking groove 210 in a close-fitting manner and at multiple points about the body 214, enhancing a strength and/or a stiffness of the attachment between the insert 202 and the attachment unit 212. As such, axial movement and/or tilting movement between the insert 202 and the attachment unit 212 are prevented or substantially limited. This advantageously helps reduce the likelihood of undesirable free play and/or slack commonly found in locking pin-type systems which can result in user discomfort and/or failure of the prosthetic socket system. It also makes the prosthetic suspension of a socket on a residual limb more reliable and less prone to failure due to movement, loading, and perspiration when compared to conventional vacuum suspension systems. Moreover, the insert 202 automatically locks in the attachment unit 212 when the insert 202 is received in the central opening 230, reducing the likelihood of user error.

According to a variation, the attachment between the insert 202 and the attachment unit 212 is arranged to provide a selected amount of free play between the insert 202 and the attachment unit 212. For instance, the attachment between the insert 202 and the attachment unit 212 can be arranged to prevent or substantially prevent relative axial movement but allow an amount of rotation or tilting between the insert 202 and the attachment unit.

When the user wants to release the insert 202 and the liner 204 from the attachment unit 212, the user can move the release mechanism 216 downward on the body 214 against the force of the one or more secondary spring members 248. If desired, the user can use the at least one button part 254 to move the release mechanism 216 downward on the body 214. This generally aligns the inclined surface 242 of the release mechanism 216 with the locking elements 234 carried by the lock body 220, providing a space or clearance for the locking elements 234 to move radially outward relative to the longitudinal axis 42. Simultaneously or nearly simultaneously, stored energy in the central spring member 228 forces the stop member 222 upwardly within the body 214, driving the locking elements 234 radially outward into engagement with the inclined surface 242 of the release mechanism 216. This advantageously helps prevent the release mechanism 216 from inadvertently moving back toward the locked position.

The prosthetic liner 204 can thus be automatically locked in the socket 32 and easily released from the socket 32 with a simple, easy, and intuitive manipulation of the release mechanism 216 on the body 214.

FIGS. 9-11 illustrate yet another embodiment of a prosthetic socket system 50. It will be appreciated that the prosthetic socket system 50 may be similar in many respects to the prosthetic socket systems 10 and 30 and may incorporate any feature described herein. The prosthetic socket system 50 can include a socket 52 having a base 58, a prosthetic liner 304, and a prosthetic attachment system 300 arranged to quickly and securely suspend the socket 52 on a residual limb donning the prosthetic liner 304. For ease of reference, the socket 52 is shown without longitudinal supports connectable to the base 58 or shell components connectable to longitudinal supports.

The attachment system 300 includes an insert 302 arranged for connection to the prosthetic liner 304, and an attachment unit 312 arranged for connection to a base 58 of the socket 52. The attachment unit 312 can be attached to the base 58 via a single fastener 313 (shown in FIG. 10).

Like in other embodiments, the attachment unit 312 includes a release mechanism 316 arranged to help move the attachment system 300 between a locked configuration in which the insert 302 is locked in the attachment unit 312 (shown in FIG. 9A) and an unlocked configuration in which the insert 302 is released from the attachment unit 312 (shown in FIG. 9B). The attachment system 300 is arranged to automatically move to the locked configuration when the insert 302 is inserted in the attachment unit 312.

Referring to FIG. 10, the attachment unit 312 includes a body 314 having a support body 318, a lock body 320 carrying a plurality of locking elements 334 that are radially repositionable relative to an axis 62 of the body 314, and a stop member 322. The support body 318 defines an opening 324 arranged for selectively receiving the stop member 322. The release mechanism 316 comprises a collar movably positioned on the body 314.

In the unlocked position, a central spring member 328 biases the stop member 322 upwardly within a central opening 330 of the body 314 such that an outer surface of the stop member 322 contacts and drives the locking elements 334 radially outward, which, in turn, engage an inclined surface 342 on the release mechanism 316. This engagement holds or maintains the release mechanism 316 in a first or down position on the body 314. One or more secondary spring members 348 are positioned between the release mechanism 316 and the support body 318. In the illustrated embodiment, the one or more secondary spring members 348 comprises a single spring member 362 with a central portion 356 of the support body 318 extending through a center of the spring member 362. The single spring member 362 helps reduce the overall size of the attachment unit 312 by at least in part accommodating the support body 318.

When the insert 302 is inserted into the central opening 330 of the lock body 320, the insert 302 exerts a downward force on the stop member 322 against the force of the central spring member 328. This permits the locking elements 334 to move radially inward and the spring member 362 to force or drive the release mechanism 316 upward along the outer surface of the body 314 toward a second or up position on the body 314. As the release mechanism 316 moves upwardly, a lower interior wall 340 of the release mechanism 316 contacts and drives the locking elements 334 radially inward relative to the axis 62 of the body 314 and into a locking groove 310 of the insert 302. This moves the attachment system 300 to the locked configuration, locking or securing the insert 302 in the attachment unit 312. As discussed above, the locking elements 334 selectively engage a locking groove 310 of the insert 302 in a close-fitting manner and at multiple points about the axis 62 of the body 314, enhancing a strength and/or a stiffness of the attachment between the insert 302 and the attachment unit 312.

According to a variation, one or more channels 380 are formed in the support body 318 that traverse the opening 324. The one or more channels 380 can have any suitable configuration but are shown comprising a single channel extending generally perpendicular to the axis of the body 314. The one or more channels 380 are arranged such that when the attachment system 300 moves toward the locked configuration or the stop member 322 moves toward the bottom of the opening 324 air is permitted to vent from the opening 324 via the one or more channels 380. This advantageously helps increase operational speed of the attachment system 300 by reducing the likelihood of an air cushion or pressure increase in the support body 318 that could slow down movement of the stop member 322 within the opening 324. In other embodiments, the one or more channels can be formed in the lock body 320 such that the channels vent the central opening 330.

When the user wishes to release the insert 302 and the liner 304 from the attachment unit 312, the user can move the release mechanism 316 downward on the body 314. This generally aligns the inclined surface 342 of the release mechanism 316 with the locking elements 334, providing a space or clearance for the locking elements 334 to move radially outward and to disengage the locking groove 310. Simultaneously or nearly simultaneously, stored energy in the central spring member 328 forces the stop member 322 upwardly along the outer surface of the body 314, driving the locking elements 334 radially inward into engagement with the inclined surface 342 of the release mechanism 316.

As shown in FIGS. 10, 11*a* and 11*b*, the attachment system 300 includes at least one manipulation feature 352 to help a user move the attachment system 300 between the locked configuration and the unlocked configuration. In the illustrated embodiment, the at least one manipulation feature 352 comprises a release handle 364 including a pair of arms 366 pivotally connected to the attachment unit 312 and a middle part 368 (shown in FIGS. 9a and 9b) extending between the arms 366. It will be appreciated that the release handle 364 can have any suitable configuration. For instance, the release handle 364 may include a single arm attached to the body 314 that wraps in part around the body 314.

The middle part 368 can be adapted to facilitate manipulation of the release handle 364. For instance, the middle part 368 can have a size corresponding to one or two fingers of a user such that a user can use one or two fingers to comfortably push down on the release handle 364, moving the attachment system 300 to the unlocked configuration. The middle part 368 can be flattened with a radial inner edge generally corresponding to the curvature of the body 314, helping to reduce the overall size, profile, and weight of the attachment system 300.

The arms 366 extend between the middle part 368 and the body 314 of the attachment unit 312. The arms 366 can be attached to the body 314 via pivot connections 370 and to the release mechanism 316 via movable connection points 374.

The pivot connections 370 can be defined by fasteners 372. The movable connection points 374 can be defined by a key or pin 376 on each arm 366 arranged to interact with slots 378 defined by the release mechanism 316. The slots 378 guide and carry the pins 376. The slots 378 can be angled or inclined relative to horizontal. In other embodiments, the slots 378 can be curved. The pin 376 is spaced from the pivot connection 370 by a distance that can be controlled to adjust the axial displacement between the release mechanism 316 and the lock body 320 described below.

As seen, the arms 366 can have an increased width proximate the body 314. For instance, each arm 366 can define an enlarged portion 381 including the pin 376 and at least part of the pivot connection 370. This helps strengthen and facilitate the connection between the arms 366 and the body 314.

When a user pushes down on the middle part 368, the release handle 364 rotates about the pivot connections 370 in a first direction. This rotation moves the pins 376 along the slots 378, which, in turn, pushes the release mechanism 316 toward the down position and the attachment system 300 toward the unlocked configuration. More particularly, sliding contact between the pins 376 and sliding contact areas 379 defined by the slots 378 pushes the release mechanism 316 downward on the body 314.

It will also be appreciated that the length of the arms 366 between the middle part 368 and the pivot connections 370 can define a moment arm that provides a user a mechanical advantage, as the release handle 364 requires less user strength to move the attachment system 300 from the locked configuration to the unlocked configuration. This advantageously improves comfort and ease of use, especially for users with limited dexterity or cognition.

When the insert 302 is inserted into the central opening 330 of the lock body 320, the spring member 362 forces or drives the release mechanism 316 upward along the outer surface of the body 314. This axial movement of the release mechanism 316 on the body 314 generates sliding contact between the pins 376 and the slots 378, which, in turn, rotates the release handle 364 about the pivot connections 370 in a second direction opposite the first direction, moving the release handle 364 back toward its original position as the attachment system 300 moves toward the locked configuration.

The release handle 364 thus provides a fast and intuitive mechanism to move the attachment system 300 from the locked configuration toward the unlocked configuration. Moreover, the release handle 364 can provide a visual indicator of the status of the attachment system 300. For instance, if the release handle 364 is up, the user can easily surmise that the attachment system 300 is in the locked configuration, and if the release handle 364 is down, the user can likewise easily surmise that the attachment system 300 is in the unlocked configuration.

It will be appreciated that the attachment unit of the present disclosure can have any suitable configuration. For instance, FIGS. 12a and 12b illustrate yet another embodiment of an attachment system 900 including a body without a distinct support body, helping to reduce the overall size and number of parts of the attachment unit. As shown, the attachment system 900 includes an insert 902 arranged for connection to a prosthetic liner and an attachment unit 912 arranged for connection to a base 98 of a socket 92.

The attachment unit 912 includes a release mechanism 916 arranged to in part move the attachment system 900 between a locked configuration in which the insert 902 is locked in the attachment unit 912, and an unlocked configuration in which the insert 902 is released from the attachment unit 912. Similar to other embodiments, the attachment system 900 can be arranged to automatically move to the locked configuration when the insert 902 is inserted in the attachment unit 912. At least one manipulation feature 952 comprising a release handle 964 is attached to the attachment unit 912 to help move the attachment system 900 between the locked and unlocked configurations.

The attachment unit 912 includes a body 914 comprising a lock body 920, and a stop member 922. The lock body 920 can be attachable to or integrated with the base 98 of the socket 92. In other words, the body 914 does not include a separate support body. This can help reduce the overall size and number of parts of the attachment unit 912, making installation and manufacturing of the attachment unit 912 simpler and easier.

At least one resilient member 926 comprising a single central spring member 928 is positioned between the stop member 922 and the base 98. The central spring member 928 is arranged to bias the stop member 922 away from the base 98. The lock body 920 carries a plurality of locking elements 934 and is supported by and/or attached to the base 98. The locking elements 934 are radially repositionable relative to an axis 95 of the body 914. The release mechanism 916 is slidably positioned on an outer surface of the body 914 such that the release mechanism 916 can be axially or vertically repositioned on the body 914 to radially reposition the locking elements 934 relative to the axis 95 of the body 914, which, in turn, moves the attachment system 900 between the locked configuration and the unlocked configuration.

In the unlocked configuration, the central spring member 928 biases the stop member 922 upwardly within a central opening 930 of the lock body 920 such that an outer surface of the stop member 922 contacts and drives the locking elements 934 radially outward relative to the axis 95 of the body 914, which, in turn, engages an inclined surface along the inner surface of the release mechanism 916.

One or more secondary spring members 948 are positioned between the base 98 and the release mechanism 916. The one or more secondary spring members 948 comprise a single secondary spring member 962 surrounding the lock body 920. The single secondary spring member 962 can be a coil spring or any other suitable resilient member. As seen, at least a portion of the single secondary spring member 962 can be positioned within an annular recess 951 defined in a bottom surface of the release mechanism 916, which, in turn, helps maintain the position of the single secondary spring member 962 within the attachment unit 912. Optionally, an annular groove 953 can be defined in the upper surface of the base 98 to help maintain the position of the single secondary spring member 962.

When the insert 902 is inserted into the central opening 930 of the lock body 920, the insert 902 exerts a downward force on the stop member 922 against the force of the central spring member 928, which, in turn, permits the locking elements 934 to move radially inward and the single secondary spring member 962 to force or drive the release mechanism 916 upward along the outer surface of the body 914 from a first position toward a second or up position. It will be appreciated that the central opening 930 of the lock body 920 is sized and configured to receive both the insert 902 and the stop member 922.

As the release mechanism 916 moves upwardly, the inner surface of the release mechanism 916 contacts and drives the locking elements 934 radially inward into a locking groove 910 of the insert 902. This moves the attachment system 900 to the locked configuration, locking or securing the insert 902 in the attachment unit 912. This advantageously helps reduce the likelihood of undesirable free play and/or slack commonly found in locking pin-type systems which can result in user discomfort and/or failure of the prosthetic socket system. It also makes the prosthetic suspension of a socket on a residual limb more reliable and less prone to failure due to movement, loading, and perspiration when compared to conventional vacuum suspension systems.

FIGS. 13a and 13b illustrate yet another embodiment of a prosthetic socket system 70. It will be appreciated that the prosthetic socket system 70 may be similar in many respects to the prosthetic socket systems 10, 30, and 50 and may include any of the features described herein. The prosthetic socket system 70 can include a socket 72, a prosthetic liner, and a prosthetic attachment system 400. The socket 72 includes a base 78, a plurality of longitudinal supports 80 connected to the base 78, and a plurality of shell components 84 connected to the longitudinal supports 80.

Similar to the other attachment systems, the attachment system 400 includes an attachment unit 412 having a body 414 comprising a support body 418 and a lock body 420. The lock body 420 defines a central opening 430 and is arranged to carry a plurality of locking elements.

A plurality of petals or prongs 482 are distributed around the central opening 430 and extend upwardly and radially outwardly from an annular flange 432. The prongs 482 can be spaced apart by spaces 484 and are sized and configured to help enhance capture of the distal end of a residual limb positioned in the socket 72. The prongs 482 form an anatomically shaped receiving space on the lock body 420 adapted to receive the distal end of a residual limb. It will be appreciated that the prongs 482 can have any suitable configuration. For instance, the prongs 482 can be overmolded on the lock body 420, integrally formed with the lock body 420, or attached to the lock body 420. The prongs 482 can be curved or rounded. The prongs 482 can have a generally triangular shape. The prongs 482 can have a generally rectangular shape or the prongs 482 can have any other suitable shape.

The prongs 482 help create a connection between the attachment unit 412 and a distal end of a prosthetic liner when the prosthetic liner is inserted in the socket 72. Moreover, the prongs 482 both engage and align the distal end of the prosthetic liner within the socket 72. The prongs 482 can thus control or help set the position of the prosthetic liner with respect to the attachment unit 412 when the liner is inserted in the socket 72, facilitating proper positioning of the prosthetic liner with respect to the attachment unit 412. This beneficially assists with donning the socket 72 for new or elderly users who may be unsure or unaware of how to properly don the socket 72, making proper use of the prosthetic socket system 70 simpler and easier.

According to a variation, the prongs 482 can have a resilient, flexible, and/or semi rigid configuration that helps the lock body 420 enhance the connection between the liner and the attachment unit 412 as the socket 72 moves between open and closed configurations. For instance, as the socket 72 moves from the open configuration toward the closed configuration, at least some of the longitudinal supports 80 and/or shell components 84 are moved or forced radially inward relative to the open configuration, decreasing a receiving volume of the socket 72 or decreasing the circumference of the socket 72. If a distal region of the shell components 84 engage with the prongs 482, the shell components 84 can force the prongs 482 radially inward onto the distal end of the residual limb positioned on the attachment unit 412, enhancing the connection between the prosthetic liner and the attachment unit 412. This beneficially can help improve prosthetic suspension and ease of use.

FIG. 14 illustrates a body 514 of a prosthetic attachment system 500 according to yet another embodiment. The body 514 comprises a lock body 520 defining a central opening 530 for receiving an insert and is arranged to carry a plurality of locking elements 534. The locking elements 534 are distributed circumferentially about an axis 501 of the body 514 and are radially repositionable relative to the axis 501. The locking elements 534 are shown comprising discrete ring segments but may be any suitable locking elements.

Similar to other embodiments, a release mechanism can be slidably positioned on the lock body 520 to move the attachment system between a locked configuration in which the locking elements 534 shift radially inward relative to the axis 501 to lock the insert in the central opening 530 and an unlocked configuration in which the locking elements 534 shift radially outward relative to the axis 501, which, in turn, releases the insert from the body 514.

In the locked configuration, the locking elements 534 can extend along lengths of the locking groove of the insert. This increases the contact area between the locking elements 534 and the body 514, which, in turn, strengthens the attachment between the insert and the body 514. This advantageously makes the attachment of the socket to the residual limb more reliable and less prone to failure.

FIG. 15 shows a prosthetic attachment system 600 according to yet another embodiment. It will be appreciated that the attachment system 600 may be similar in many respects to the attachment systems 100, 200, 300, 400, and 500. The attachment system 600 includes an insert 602 arranged to be connected to a prosthetic liner and an attachment unit 612 comprising a distal portion of a socket 601. The socket 601 can be a conventional socket that is rigid and has a general uniform shape. In other embodiments, the socket 601 can be an adjustable socket.

The insert 602 includes an outer radial surface defining a circumferential locking groove 610 and an upper surface arranged to engage a distal end of the liner. The insert 602 can be connected to the liner in any suitable manner. The attachment unit 612 comprises a body 614 defining a central opening 630 sized and configured to receive the insert 602. The body 614 can exhibit any suitable shape and can be integral to the socket 601 or can be separate from and attached to the socket 601.

A plurality of locking elements 634 are mounted or otherwise attached to the body 614 within at least one recess or groove 686 formed in a sidewall of the central opening 630. The locking elements 634 can be any suitable locking elements but are shown as wheel members or ball bearings. The locking elements 634 can be made of any suitable material.

Similar to other embodiments, the attachment system 600 is movable between an unlocked configuration and a locked configuration (shown in FIG. 15) in which the locking elements 634 are received in the locking groove 610, locking the insert 602 in the body 614. As shown, spring members 688 are located in the at least one recess 686 and bias the locking elements 634 radially inward and into the central opening 630. As the insert 602 is inserted downward into the central opening 630, the outer radial surface of the insert 602 engages and forces the locking elements 634 radially outward into the at least one recess 686, which, in turn, compresses the spring members 688. According to a variation, the outer radial surface of the insert 602 rotates the locking elements 634 as the insert 602 is moved downward through the central opening 630, making insertion of the inert 602 in the central opening 630 easier.

When the locking groove 610 of the insert 602 is axially positioned in general alignment with the locking elements 634, stored energy in the spring members 688 drives the locking elements 634 into the locking groove 610, automatically and securely locking the insert 602 in the attachment unit 612. Optionally, the insert 602 is sized and configured such that the locking elements 634 lock in the locking groove 610 when a bottom of the insert 602 is at or near a bottom of the central opening 630. It will be appreciated that the attachment system 600 includes a release mechanism adapted to selectively release the locking elements 634 from the locking groove 610.

FIGS. 16 and 17 illustrate an insert 702 for use in a prosthetic attachment system 700 according to another embodiment of the present disclosure. The insert 702 includes an outer radial surface defining a circumferential locking groove 710 and an upper surface arranged for connection to a distal end 703 of a prosthetic liner 704. The upper surface of the insert 702 can have a concave shape or any other suitable shape. A bottom surface of the insert 702 defines an opening 790 arranged to receive a fastener 792 that threadedly attaches the insert 702 to the distal end 703 of the prosthetic liner 704. The opening 790 can include a counter bore 794 for accommodating a head portion of the fastener 792.

As shown, a spacer 796 is located between the insert 702 and the distal end 703 of the prosthetic liner 704. A bottom surface of the spacer 796 defines an opening 798 for receiving the fastener 792 and/or a connecting portion 701 of the prosthetic liner 704.

The insert 702 includes at least one positioning feature for generating an amount of play or movement in the attachment between the insert 702 and the prosthetic liner 704. This selected amount of play or movement advantageously allows a user to more easily position the insert 702 in an attachment unit of the present disclosure and/or locate the attachment unit, facilitating donning of a prosthetic socket. In the illustrated embodiment, the at least one positioning feature comprises the opening 790 of the insert 702 being oversized relative to a shaft portion 705 of the fastener 792. More particularly, a diameter of the opening 790 is greater than a diameter of the shaft portion 705. The oversized opening 790 in combination with the concave shape of the upper surface of the insert 702 allows the insert 702 to float or move from side to side on the spacer 796. The play or movement in the connection between the insert 702 and the prosthetic liner 704 beneficially allows at least some self-alignment or adjustment of the insert 702 while being inserted into an attachment unit, making donning of a prosthetic socket system easier.

FIGS. 18-20 illustrate an insert 1002 including at least one positioning feature according to another embodiment. The insert 1002 includes an outer radial surface defining a circumferential locking groove 1010 and an upper surface 1003 for connection to a distal end of a prosthetic liner. The upper surface 1003 can have a concave shape or any other suitable shape. An opening 1090 is defined in the insert 1002 for receiving a fastener 1092 arranged to attach the insert 1002 to the prosthetic liner. The opening 1090 can include a lower portion 1094 arranged to engage with a head portion 1098 of the fastener 1092, and an upper portion 1096 arranged to receive a connecting portion of the prosthetic liner.

The insert 1002 includes at least one positioning feature for facilitating insertion of the insert 1002 in an attachment unit of the present disclosure. The at least one positioning feature comprises one or more deformable members arranged to provide an amount of play or self-adjustment in the connection between the insert 1002 and a prosthetic liner via deformation. The one or more deformable members can include a first deformable member 1005 located on the upper surface 1003 of the insert 1002, and a second deformable member 1007 locating in the lower portion 1094 of the opening 1092.

The first deformable member 1005 is arranged to engage with the distal end of the prosthetic liner and deform between the insert 1002 and the distal end of the prosthetic liner, which, in turn, allows for a small amount of movement or angular misalignment between the insert 1002 and the distal end of the prosthetic liner. The second deformable member 1007 is arranged to engage with the head portion 1098 of the fastener 1092 and deform between the insert 1002 and the fastener 1092, which, in turn, allows for a small amount of movement or angular misalignment between the insert 1002 and the fastener 1092 and the distal end of the prosthetic liner. The play provided by the first and/or second deformable members 1005, 1007 in the connection between the insert 1002 and the prosthetic liner advantageously allows at least some self-alignment or adjustment of the insert 1002 while being inserted into the attachment unit, facilitating donning of a prosthetic socket system.

The deformable members 1005, 1007 can be separate from and attached to the insert 1002. In other embodiments, the deformable members 1005, 1007 can be overmolded onto the insert 1002. The deformable members 1005, 1007 can be made of elastomeric material, foam material, or any other suitable material. The deformable members 1005, 1007 can be resilient. The deformable members 1005, 1007 can comprise gaskets, rings, ring segments, bars, or any other suitable members.

According to a variation, the deformable members 1005, 1007 can be formed of one or more different materials selected to vary the amount of movement or play created between the insert 1002 and the prosthetic liner and/or fastener 1092. For instance, the deformable members 1005, 1007 can be formed with materials having greater durometers to reduce the amount of deformation of the deformable members 1005, 1007. The deformable members 1005, 1007 can be selected based on a size or dimension to vary the amount of movement or play created between the insert 1002 and the prosthetic liner and/or fastener 1092. By way of example, a deformable member having a greater cross-sectional diameter may be selected to provide more movement or play than a different deformable member having a smaller cross-sectional diameter.

FIGS. 21 and 22 illustrate an insert 1102 including at least one positioning feature according to another embodiment. The insert 1102 includes an outer radial surface defining a circumferential locking groove 1110 and an upper surface arranged for connection to a distal end of a prosthetic liner. An opening 1190 is defined in the insert 1102 for receiving a fastener 1192 arranged to attach the insert 1102 to the prosthetic liner.

The insert 1102 includes at least one positioning feature for facilitating insertion of the insert 1102 in an attachment unit of the present disclosure. The at least one positioning feature comprises a rotating joint 1111 positionable in the opening 1190 of the insert 1102. The rotating joint 1111 defines a through hole for receiving the fastener 1192 and interacts with the fastener 1192. The rotating joint 1111 is arranged to allow a small or limited amount of rotation or play between the fastener 1192 and the insert 1102, which, in turn, provides a small or limited amount of rotation or play between the prosthetic liner and the insert 1102. The play provided by the rotating joint 1111 in the connection between the insert 1102 and the prosthetic liner advantageously allows at least some self-alignment or adjustment of the insert 1102 while being inserted into the attachment unit, facilitating donning of a prosthetic socket system. It will be appreciated that the rotating joint 1111 can comprise a swivel joint, a spherical bearing, or any other suitable rotating joint. The rotating joint 1111 may be formed of plastic material, metal, combinations thereof, or any other suitable material.

FIGS. 23-25 illustrate yet another embodiment of a prosthetic socket system 800. It will be appreciated that the prosthetic socket system 800 may be similar in many respects to the prosthetic socket systems described above. The prosthetic socket system 800 can include socket 801, a prosthetic liner 804, and a prosthetic attachment system 805. The socket 801 includes a base 807 and a plurality of longitudinal supports 809 connected to the base 807. The attachment system 805 includes an insert 811 arranged for connection to the prosthetic liner 804 and an attachment unit 813 integrated with the base 807.

The insert 811 can be made of any suitable material. The material selection can depend on desired function. The insert 811 can include an elastomeric polymer arranged to provide cushioning to a distal end of a residual limb. The insert 811 can include a plastic material having a stiff configuration, enhancing the durability of the insert 811.

Referring to FIG. 24, the insert 811 can define a through-hole 815 for receiving and accommodating a fastener 817. An upper surface of the insert 811 can define a concave surface arranged to engage or fit on the distal end of the prosthetic liner 804.

The insert 811 includes one or more magnets 820 and/or ferromagnetic material. The magnets 820 can be disposed in one or more openings 819 formed in the upper surface of the insert 811. This allows the magnets 820 to be concealed by the insert 811 when the insert 811 is attached to the prosthetic liner 804 (see FIG. 18). In other embodiments, the magnets 820 can be attached to the outer surface of the insert 811 or incorporated into the material forming the insert 811.

As seen in FIG. 25, the attachment unit 813 includes one or more magnets 822 and/or ferromagnetic material. The magnets 822 are arranged to create a magnetic connection between the prosthetic liner 804 (shown in FIG. 18) and the socket 801 when the prosthetic liner 804 is inserted into the socket 801. The attachment unit 813 defines a through opening 821 arranged to receive and accommodate a conventional locking pin. The attachment unit 813 includes a base part 823 and a removable part 825 attached to the base part 823. The magnets 822 can include permanent magnets disposed in openings 827 defined in the removable part 825.

When the prosthetic liner 804 is inserted into the socket 801, the distal end of the prosthetic liner 804 is held against the attachment unit 813 by magnetic attraction between the insert 811 and the attachment unit 813. This beneficially secures the prosthetic liner 804 to the socket 801, improving suspension of the socket 801 on the residual limb.

The magnetic attraction between the insert 811 and the attachment unit 813 can also or alternatively help ensure a proper or correct positioning of the prosthetic liner 804 in the socket 801. Proper positioning of the prosthetic liner 804 provides a good, comfortable fit and helps prevent or limit undesirable pistoning of the residual limb within the socket 801. It can also help ensure that the length of the socket 801 is sized or adjusted to fit the residual limb.

According to a variation, the magnetic force or attraction between the insert 811 and the attachment unit 813 can be customized based on the individual needs of the user. For example, the magnetic strength of the magnets 820, 822 can be selected based on activity level. The level of magnetic force can be adjusted by varying the number of magnets and/or the strength of the magnets 820. In other embodiments, the amount of magnetism can be varied by a clinician or user by adding more or less magnets or altering the position of the magnets 820, 822 such as in a modular fashion.

It will be appreciated that the magnetic attraction between the insert 811 and the attachment unit 813 can be adapted for pure suspension (similar to a locking pin or lanyard) or to maintain the distal end of the prosthetic liner 804 in a specific position relative to the base 807 of the socket 801. The magnetic attraction between the insert 811 and the attachment unit 813 can also be an alternative to or used in combination with different attachment or tensioning systems.

Optionally, a hardness of the insert 811 can be selected to produce a click or knock when it contacts the attachment unit 813, providing audible feedback to the user that the prosthetic liner 804 is correctly or properly positioned in the socket 801.

While various aspects and embodiments have been disclosed herein, other aspects and embodiments are contemplated. For instance, in other embodiments, the insert can be attached to the socket and the attachment unit can be attached to the prosthetic liner. Moreover, the insert is shown as being attached to the distal end of the prosthetic liner but can be attached to any suitable portion of the liner.

In other embodiments, the attachment unit can be arranged such that movement of the release mechanism in an upward direction or away from the base part moves the attachment system toward the unlocked position, releasing the insert. Optionally, the attachment system may include a strap or tab attached to the release mechanism. The strap or tab can be made of fabric and arranged so that when a user pulls on the strap or tab, the attachment system moves toward the unlocked position. This beneficially requires less dexterity from the user.

In other embodiments, the attachment system of the present disclosure can be operatively connected to a tensioning system of the socket. This can allow for movement of the release mechanism toward the unlocked position to trigger a release of tension in the tensioning system, or movement of the release mechanism toward the locked position to trigger an increase in tension in the tensioning system. This can encourage a user to follow a sequence of steps when doffing or donning the socket, which can benefit users with poor cognition. For instance, this can encourage a user donning the socket to lock the insert into the attachment unit before tensioning the tensioning system. This arrangement can also decrease risk of injury to the user as the user cannot use the socket unless it is correctly or properly secured to the liner.

By providing a prosthetic attachment system as shown and described herein, the problems of existing attachment systems being difficult to operate, leading to incorrect usage, noise, and safety issues, is overcome by providing a more intuitive, forgiving, and simple connection between a prosthetic liner and the corresponding socket that facilitates accurate and secure attachment.

The various aspects and embodiments disclosed herein are for purposes of illustration and are not intended to be limiting. Additionally, the words "including," "having," and variants thereof (e.g., "includes" and "has") as used herein, including the claims, shall be open ended and have the same meaning as the word "comprising" and variants thereof (e.g., "comprise" and "comprises").

The invention claimed is:

1. A prosthetic attachment system comprising:
an insert arranged for connection to a closed distal end of a prosthetic liner;
an attachment unit arranged for connection to a distal end of a prosthetic socket, the attachment unit comprising a body defining an axis and a central opening for selectively receiving the insert;
a plurality of locking elements carried by the body, the plurality of locking elements being circumferentially distributed about the axis and radially repositionable relative to the axis;
wherein the attachment unit includes a stop member arranged such that when the prosthetic attachment system is in an unlocked configuration an outer surface of the stop member engages the plurality of locking elements;
wherein the body includes a lock body carrying the plurality of locking elements and defining the central opening, at least one resilient member arranged to bias the stop member upwardly within the central opening;
further comprising a release mechanism slidably repositionable on an outer surface of the body to move the prosthetic attachment system between a locked configuration in which the plurality of locking elements are radially repositioned to lock the insert in the central opening and the unlocked configuration in which the insert is released from the central opening;
wherein when the prosthetic attachment system is in the locked configuration the release mechanism drives the plurality of locking elements radially inward into engagement with a circumferential locking groove on the insert to lock the insert in the central opening of the body;
wherein the release mechanism defines an inner surface having a lower interior wall arranged to engage the plurality of locking elements in the locked configuration and an inclined surface that extends upwardly and radially outward from the lower interior wall, the inclined surface arranged to engage the plurality of locking elements in the unlocked configuration.

2. The prosthetic attachment system of claim 1, wherein the stop member is arranged to drive the plurality of locking elements radially outward into engagement with the inclined surface of the release mechanism.

3. The prosthetic attachment system of claim 1, wherein when the prosthetic attachment system is in the locked configuration the lower interior wall of the release mechanism drives the plurality of locking elements radially inward into engagement with a circumferential locking groove of the insert.

4. The prosthetic attachment system of claim 3, wherein the engagement between the plurality of locking elements and the inclined surface of the release mechanism is configured to hold the prosthetic attachment system in the unlocked configuration.

5. The prosthetic attachment system of claim 1, wherein the release mechanism includes at least one manipulation feature arranged to assist a user in moving the release mechanism on the body.

6. The prosthetic attachment system of claim 1, wherein the at least one resilient member comprises a plurality of spring members distributed circumferentially about the axis.

7. The prosthetic attachment system of claim 6, wherein the at least one resilient member comprises a central spring member.

8. The prosthetic attachment system of claim 1, wherein the body defines an annular flange surrounding the central opening, the annular flange arranged to direct the insert into the central opening when the prosthetic liner is inserted into the prosthetic socket.

9. The prosthetic attachment system of claim 1, wherein the insert is removably attachable to the closed distal end of the prosthetic liner.

10. The prosthetic attachment system of claim 1, wherein the attachment unit is removably attachable to the distal end of the prosthetic socket.

11. The prosthetic attachment system of claim 1, wherein the plurality of locking elements comprise ball bearing elements.

12. A prosthetic attachment system comprising:
an insert arranged for connection to a closed distal end of a prosthetic liner;
an attachment unit arranged for connection to a distal end of a prosthetic socket, the attachment unit comprising a body defining an axis and a central opening for selectively receiving the insert;
at least one locking element carried by the body located about the axis and repositionable relative to the axis;
wherein the attachment unit includes a stop member arranged such that when the prosthetic attachment system is in an unlocked configuration an outer surface of the stop member engages the at least one locking element
wherein the body includes a lock body carrying the plurality of locking elements and defining the central opening, at least one resilient member arranged to bias the stop member upwardly within the central opening;

wherein a release mechanism is located on an outer surface of the body to move the prosthetic attachment system between a locked configuration to lock the insert in the central opening and an unlocked configuration in which the insert is released from the central opening;

wherein when the prosthetic attachment system is in the locked configuration the release mechanism drives the at least one locking element radially inward into engagement with a circumferential locking groove on the insert to lock the insert in the central opening of the body;

wherein the release mechanism defines an inner surface having a lower interior wall arranged to engage the at least one locking element in the locked configuration and an inclined surface that extends upwardly and radially outward from the lower interior wall, the inclined surface arranged to engage the at least one locking element in the unlocked configuration.

13. The prosthetic attachment system of claim 12, wherein the release mechanism includes at least one manipulation feature arranged to assist a user in moving the release mechanism on the body.

14. The prosthetic attachment system of claim 12, wherein when the prosthetic attachment system is in the locked configuration the lower interior wall of the release mechanism drives the at least one locking element radially inward into engagement with a circumferential locking groove of the insert.

15. A prosthetic attachment system comprising:

an insert arranged for connection to a closed distal end of a prosthetic liner;

an attachment unit arranged for connection to a distal end of a prosthetic socket, the attachment unit comprising a body defining an axis and a central opening for selectively receiving the insert;

a plurality of locking elements carried by the body, the plurality of locking elements being circumferentially distributed about the axis and radially repositionable relative to the axis;

wherein the attachment unit includes a stop member arranged such that when the prosthetic attachment system is in an unlocked configuration an outer surface of the stop member engages the plurality of locking elements;

wherein the body includes a lock body carrying the plurality of locking elements and defining the central opening, at least one resilient member arranged to bias the stop member upwardly within the central opening;

wherein the at least one resilient member comprises a plurality of spring members distributed circumferentially about the axis;

further comprising one or more secondary spring members arranged to bias the prosthetic attachment system toward the unlocked configuration.

* * * * *